(12) United States Patent
Stewart, Jr. et al.

(10) Patent No.: US 7,973,213 B2
(45) Date of Patent: Jul. 5, 2011

(54) ANTIBIOTIC RESISTANCE CONFERRED BY A PLANT ABC TRANSPORTER GENE WHEN EXPRESSED IN TRANSGENIC PLANTS

(75) Inventors: C. Neal Stewart, Jr., Knoxville, TN (US); Mentewab Ayalew, Atlanta, GA (US)

(73) Assignee: University of Tennessee Research Foundation, Knoxville, TN (US)

( * ) Notice: Subject to any disclaimer, the term of this patent is extended or adjusted under 35 U.S.C. 154(b) by 659 days.

(21) Appl. No.: 11/912,713

(22) PCT Filed: Nov. 9, 2006

(86) PCT No.: PCT/US2006/016447
§ 371 (c)(1),
(2), (4) Date: Jun. 9, 2008

(87) PCT Pub. No.: WO2006/119110
PCT Pub. Date: Nov. 9, 2006

(65) Prior Publication Data
US 2008/0250527 A1 Oct. 9, 2008

Related U.S. Application Data

(60) Provisional application No. 60/676,476, filed on Apr. 29, 2005, provisional application No. 60/712,456, filed on Aug. 30, 2005.

(51) Int. Cl.
*A01H 1/00* (2006.01)
*A01H 5/00* (2006.01)
*C12N 5/14* (2006.01)

(52) U.S. Cl. ........ 800/278; 800/298; 435/410; 536/23.6

(58) Field of Classification Search .................. None
See application file for complete search history.

(56) References Cited

U.S. PATENT DOCUMENTS

2007/0074313 A1* 3/2007 Rommens et al. ............ 800/288

OTHER PUBLICATIONS

Theodoulou et al., Review, Plant ABC transporters, Biochimica et Biophysica Acta, 2000, pp. 79-103, vol. 1465.*
Klein et al, The Plant Journal, 2003, vol. 33, pp. 119-129.*
Database PIR_80, Accession No. T47652, publication date Apr. 20, 2000.*
Database PIR_80, Accession No. T47648, publication date Apr. 20, 2000.*
Database GenEmbl Accession No. AL132954, publication date Nov. 15, 1999.*
Database GenEmbl, Accession No. AL132970, publication date Nov. 15, 1999.*
Sanchez-Fernandez, R. et al., "The *Arabidopsis thaliana* ABC Protein Superfamily, a Complete Inventory", *The Journal of Biological Chemistry*, Aug. 10, 2001, pp. 30231-30244, vol. 276, No. 32, The American Society for Biochemistry and Molecular Biology, Inc.
Higgins, C.F., "ABC Transporters: from Microorganisms to Man", *Annu. Rev. Cell Biol.*, 1992, pp. 67-113, vol. 8, Annual Reviews Inc.
Kolukisaoglu, H.U. et al., "Family business: the multidrug-resistance related protein (MRP) ABC transporter genes in *Arabidopsis thaliana*", *Planta*, Nov. 2002, pp. 107-119, vol. 216, Springer-Verlag.
Liu, G. et al., "Enhanced Multispecificity of *Arabidopsis* Vacuolar Multidrug Resistance-associated Protein-type ATP-binding Cassette Transporter, AtMRP2", *The Journal of Biological Chemistry*, Mar. 23, 2001, pp. 8648-8656, vol. 276, No. 12, The American Society for Biochemistry and Molecular Biology, Inc.
Mentewab, A. et al., "Overexpression of an *Arabidopsis thaliana* ABC transporter confers kanamycin resistance to transgenic plants", *Nature Biotechnology*, Sep. 2005, pp. 1177-1180, vol. 23, No. 9, Nature Publishing Group.

* cited by examiner

*Primary Examiner* — Eileen B O Hara
(74) *Attorney, Agent, or Firm* — Saliwanchik, LLoyd & Eisenschenk

(57) ABSTRACT

The use of selectable marker genes, such as the kanamycin resistance encoding neomycin phosphotransferase (nptII), has been invaluable in transgenic plant production. The subject invention provides a new selectable marker gene, an *Arabidopsis thaliana* ATP binding cassette (ABC) transporter, Atwbc19 and methods of using the gene for the identification of transgenic plants. Since ABC transporters are endogenous to plants, there should be less controversy using Atwbc19, as a selectable marker in transgenic plants with regards to concerns of horizontal gene transfer.

12 Claims, 8 Drawing Sheets

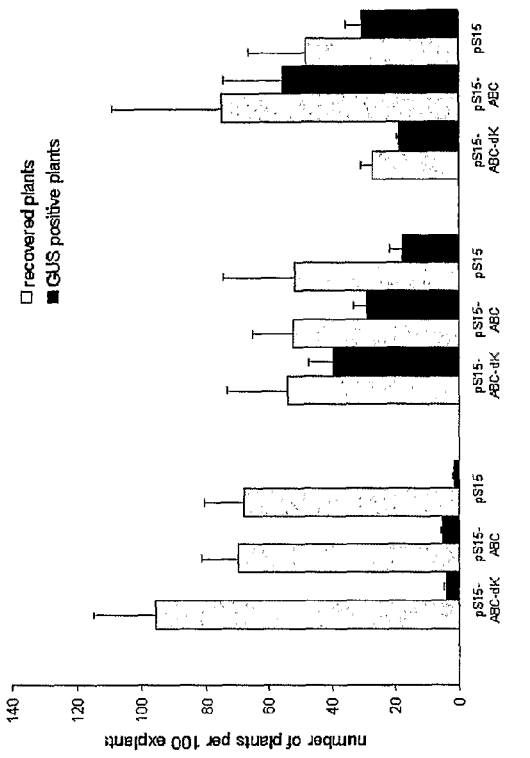
FIGURE 1A
FIGURE 1B
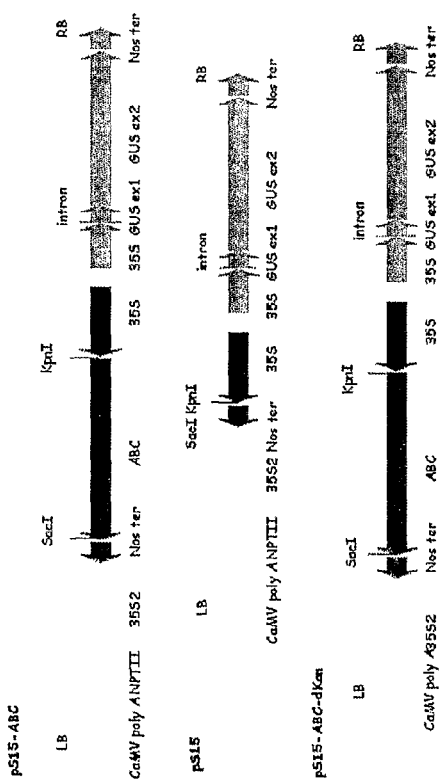
FIGURE 1C

FIGURE 2A    FIGURE 2B
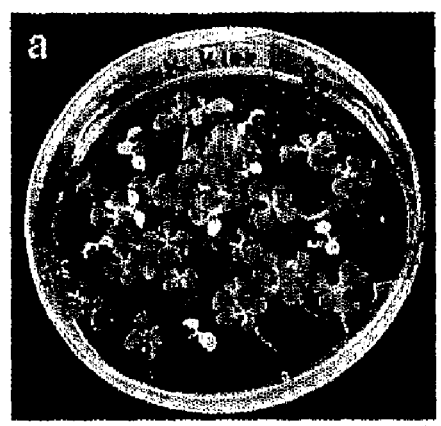
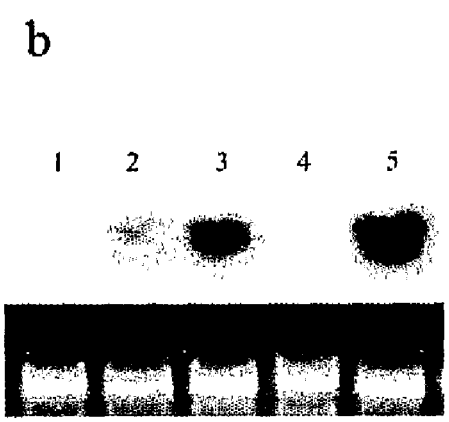
FIGURE 2C

ANTIBIOTIC RESISTANCE CONFERRED BY A PLANT ABC TRANSPORTER GENE WHEN EXPRESSED IN TRANSGENIC PLANTS

CROSS REFERENCE TO RELATED APPLICATIONS

This application is the U.S. national stage application of International Patent Application No. PCT/US2006/016447, filed Apr. 28, 2006, which claims the benefit of the U.S. Provisional Application No. 60/676,476, filed Apr. 29, 2005, and U.S. Provisional Patent Application No. 60/712,456, filed Aug. 30, 2005, the disclosures of which are hereby incorporated by reference in their entireties, including all figures, tables and amino acid or nucleic acid sequences.

Portions of this invention were made with government support under a grant entitled, "Plants That Detect Landmines", issued by the Science Applications International Corporation on behalf of the U.S. Army (government contract number 01-0613-31-1692-011 (2002-2004). The U.S. government may have certain rights in this invention.

BACKGROUND OF THE INVENTION

The use of selectable marker genes, such as the kanamycin resistance encoding neomycin phosphotransferase (nptII), has been invaluable in transgenic plant production. Since all currently used antibiotic resistance genes are from bacterial origin, there have been concerns about horizontal gene transfer from transgenic plants to microbes thereby causing new antibiotic resistance problems. Here we characterize the first, to our knowledge, plant gene shown to confer antibiotic resistance in transgenic plants: an *Arabidopsis thaliana* ATP binding cassette (ABC) transporter, Atwbc19. Its mechanism of conferring resistance is novel while the level of endowed resistance is comparable to that of bacterial antibiotic resistance genes in transgenic tobacco using the 35S promoter. Thus, since ABC transporters are endogenous to plants, there should be less controversy using Atwbc19, as a selectable marker in transgenic plants with regards to concerns of horizontal gene transfer.

ABC proteins are biologically ubiquitous proteins classified on the basis of the presence of an ATP-binding cassette or nucleotide binding folds, with sharing of 30-40% identity between family members (Higgins, 1992). The vast majority of ABC-transporters are membrane bound and contain transmembrane domains (TMDs). These TMDs are considered to form the pathway for solute movement across the phospholipid bilayer and appear to determine, or at least contribute to, the substrate selectivity of the transporter. Resistance of human cancer cells to chemotherapeutic agents and multidrug resistance in infectious microorganisms often arises from the over-expression of ABC transporters. Their clinical significance has spurred a number of structural studies to better understand how ATP hydrolysis is coupled with a substrate specific transport.

Among all multicellular organisms sequenced so far, plants have the largest number of ABC proteins encoded in their genome. Why plants allocate proportionally more genes to this superfamily relative to their genome size is not clear, but begs the question of adaptive significance (Sanchez-Fernandez et al., 2001a). *Arabidopsis* ABC transporters have been classified on the basis of their domain organization and their homology to orthologous genes, but their functions remain largely unknown (Sanchez-Fernandez et al., 2001b). The AtWBC family (White-Brown Complex homologues) is the largest of all *Arabidopsis* ABC transporters with 29 members. One recent publication attributes the role of Atwbc12 to the secretion of cuticular wax (Pighin et al., 2004).

Kanamycin is an aminoglycoside antibiotic isolated from the soil bacterium *Streptomyces kanamyceticus*. Aminoglycosides act primarily by binding to the 30S subunit of prokaryotic ribosomes and inhibiting protein synthesis (Mingeot-Leclercq et al., 1999). In eukaryotes they inhibit protein synthesis by putative non-specific binding to the ribosomal complex, hence their usefulness as selection agents for plant and mammalian genetic transformation. In bacteria, aminoglycoside resistance is most often associated with the presence of inactivating enzymes. These enzymes, classified as aminoglycoside acetyltransferases, nucleotidyltransferases or phosphotransferases, catalyze the transfer of acetyl, adenosine monophosphate, or phosphate groups onto the aminoglycoside antibiotics (Wright et al., 1998). Neomycin phosphotransferase type II (nptII), originally isolated from the Tn5 transposon of *Escherichia coli*, is among enzymes of the latter group. Since its first use in 1983 (Bevan et al., 1983; Fraley et al., 1983; Herrera-Estrella et al., 1983), it has been the most commonly used selectable marker for the production of transgenic plants. The fact that kanamycin resistance via aminoglycoside modifying enzymes is common among soil bacteria has contributed to its acceptance by regulatory agencies for deregulated transgenic plants containing nptII.

BRIEF DESCRIPTION OF THE DRAWINGS

FIGS. 1A-1C. Use of Atwbc19 as a selection marker. FIG. 1A: T-DNA region of constructs used for transformation. RB: right border, LB: left border, I: bean catalase intron. FIG. 1B: Comparison of tobacco transformation efficiency using the 3 different plasmids and 3 kanamycin selection regimes. Stars indicate significant differences from pS15-ABC-dKan plasmid at the corresponding kanamycin selection regime (t-test, $P<0.05$). FIG. 1C: Southern blot analysis of 12 putative $T_0$ plants selected with 100 mg/l kanamycin from each construct. DNA was extracted from $T_0$ plants and digested with KpnI and SacI, such that hybridizations with $^{32}$P-labeled Atwbc19 probe would produce a 2.1 kb fragment. M: marker, 25 ng: 25 ng pS15-ABC plasmid, 50 ng: 50 ng pS15-ABC plasmid, C: Nontransgenic tobacco control. Numbers indicate putative transgenic events.

FIGS. 2A-2C. Kanamycin resistance of $T_1$ transgenic plants transformed with pS15-ABC-dKan. FIG. 2A: Segregation of $T_1$ seeds from transgenic event 30 plated on media with 200 mg/l kanamycin. FIG. 2B: Expression of Atwbc19 is confirmed by northern blot analysis. Lane 1: Nontransgenic tobacco control); lanes 2-5 pS15-ABC-dKan transgenic events 27, 28, 26, 30. Bottom: 18S ribosomal RNA hybridization is shown for equal loading. FIG. 2C: Root growth of $T_1$ seeds from transgenic events 28 and 30 plated on media with 200 mg/l kanamycin.

FIG. 3C: represents a magnified version of (FIG. 3B): epifluorescence detection of GFP in vacuoles. Note that fluorescence is excluded from the nucleus. Bar=30 µm. FIGS. 3D-F: confocal laser scanning microscope detection of GFP fluorescence in protoplast (top left) and vacuole (fainter, lower right) in the green, red and merged channels. GFP is apparently localized in the vacuolar lumen and is excluded from nuclei. Bar-20 µm.

FIG. 5. ClustalW alignment of the *Arabidopsis thaliana* WBC members most closely related to Atwbc19. Atwbc18, Atwbc17 and Atwbc16 share respectively 85%, 80% and 76% peptide similarity with Atwbc19. The conserved regions of the ABC domain (Walker A, Walker B and ABC signature) and the transmembrane domains (TMD1-6) are indicated.

FIG. 6A: root growth on vertical MS media containing 100 mg/l kanamycin, 2 weeks after germination. FIG. 6B: NPTII synthesis levels as measured by ELISA assays in roots and shoots. Bars indicate standard deviations.

BRIEF DESCRIPTION OF THE SEQUENCES

Figures 3A, 3B, 3C, 3D, 3E, 3F:
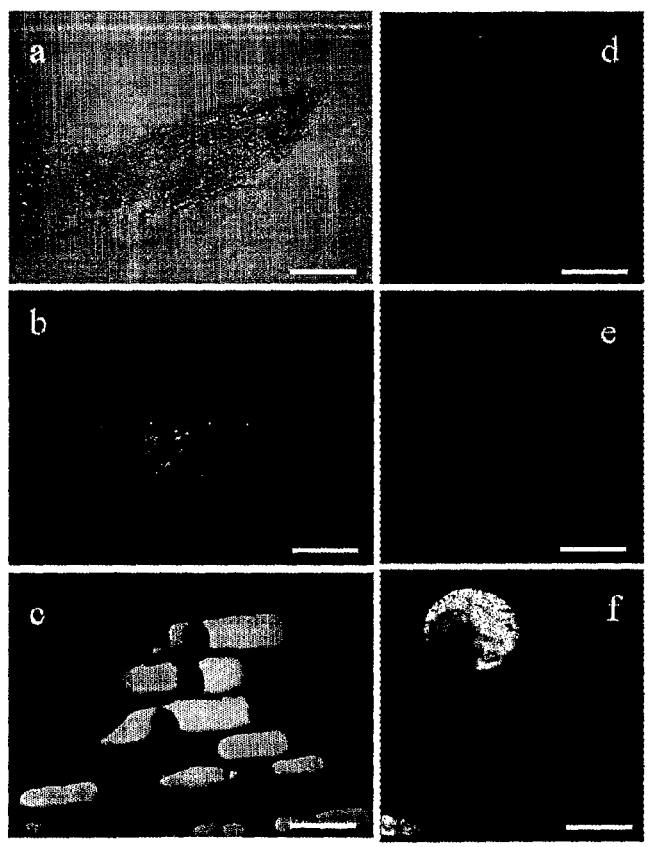
FIGS. 3A-F. Subcellular localization of Atwbc19: Fluorescence detection from an N-terminal GFP fusion protein. White light (FIG. 3A) and epifluorescence (FIG. 3B) microscope detection of GFP in root tip cells. Bar=2 mm.

SEQ ID NO: 1 is an exemplary sequence encoding the Atwbc19 polypeptide. The segment of the polynucleotide sequence that encodes the Atwbc19 polypeptide is located at positions 103-2280 of SEQ ID NO: 1.

SEQ ID NO: 2 is the amino acid sequence of the Atwbc 19 polypeptide.

SEQ ID NOs: 3-4 illustrate a CDS representation of Atwbc19 polynucleotide and polypeptide sequences.

SEQ ID NOs: 5-6 are a CDS representation of the Atwbc16 polynucleotide and polypeptide sequences.

DETAILED DISCLOSURE OF THE INVENTION

The subject invention provides a method of imparting kanamycin resistance to a plant, plant cell, or plant part susceptible to kanamycin comprising:
a) obtaining a plant, plant cell, or plant part that is susceptible or sensitive to kanamycin; and
b) transforming said plant, plant cell, or plant part with Atwbc19 (SEQ ID NOs: 1 or 3), Atwbc16 (SEQ ID NO: 5) or homologs thereof or a fragment of Atwbc19, Atwbc16 or homologs thereof that encodes a functional fragment of the transporter polypeptide.

The subject invention provides a method of screening transgenic plants, plant cells or plant parts comprising:
a) growing a transformed plant, plant cell, or plant part containing the Atwbc19 (SEQ ID NO: 1 or 3), Atwbc16 (SEQ ID NO: 5) or homologs thereofor a fragment of Atwbc19, Atwbc16 or homologs thereof that encodes a functional fragment of the transporter polypeptide on kanamycin containing media; and
b) identifying kanamycin resistant plants, plant cells, or plant parts.

The subject invention provides a method of imparting kanamycin resistance to a plant, plant cell, or plant part susceptible to kanamycin comprising:
a) obtaining a plant, plant cell, or plant part that is susceptible or sensitive to kanamycin; and
b) transforming said plant, plant cell, or plant part with a heterologous promoter that is operably linked to an endogenous Atwbc19 gene (SEQ ID NO: 1 or 3), Atwbc16 (SEQ ID NO: 5) a functional equivalent or homolog of endogenous Atwbc19 or Atwbc16, or a fragment of Atwbc19 or Atwbc16 (or said functional equivalent) that encodes a functional fragment of the transporter polypeptide.

The subject invention provides a method of screening transgenic plants, plant cells or plant parts comprising:
a) growing a transformed plant, plant cell, or plant part comprising a heterologous promoter operably linked to the Atwbc19 gene (SEQ ID NO: 1) or Atwbc16 (SEQ ID NO: 5), or a functional equivalent of the Atwbc19 or Atwbc16 gene, a functional equivalent or homolog of Atwbc19 or Atwbc16, or a fragment of Atwbc19 or Atwbc16 that encodes a functional fragment of the transporter polypeptide or its functional equivalent (homolog) on kanamycin containing media; and
b) identifying kanamycin resistant plants, plant cells, or plant parts.

In the context of the subject invention, the phrases "functional fragment", "biologically active fragment" or "active fragment" can be used interchangeably. Further, these phrases are defined, in the context of this invention, as providing the ability to confer kanamycin resistance in plants, plant cells, or plant parts that are not resistant to kanamycin in their naturally occurring form (i.e., a non-transformed plant, non-transformed plant cell, or non-transformed plant part).

In addition to the Atwbc19 or Atwbc16 polynucleotide sequences and functional fragments thereof, the subject invention (e.g., screening of transgenic plants or conferring kanamycin resistance on kanamycin sensitive plants) can also be practiced with genes homologous to Atwbc19 or Atwbc16 and homologous functional fragments of Atwbc19 or Atwbc16. Homologs of the Atwbc19 or Atwbc16 also include nucleotide sequences that encode the Atwbc19 or Atwbc16 polypeptides (or fragments thereof) identified in SEQ ID NOs: 2, 4 or 6. In this aspect of the a homologous polynucleotide or polypeptide sequence, for the purposes of the present invention, encompasses a sequence having a percentage identity with the polynucleotide or polypeptide sequences, set forth herein, of between at least (or at least about) 20.00% to 99.99% (inclusive) and the ability to confer kanamycin resistance on a transformed plant, plant cell or plant part. The aforementioned range of percent identity is to be taken as including, and providing written description and support for, any fractional percentage, in intervals of 0.01%, between 20.00% and, up to, including 99.99%. These percentages are purely statistical and differences between two nucleic acid sequences can be distributed randomly and over the entire sequence length. For example, homologous sequences can exhibit a percent identity of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent with the sequences of the instant invention. Typically, the percent identity is calculated with reference to the fall length, native, and/or naturally occurring polynucleotide. The terms "identical" or percent "identity", in the context of two or more polynucleotide or polypeptide sequences, refer to two or more sequences or subsequences that are the same or have a specified percentage of amino acid residues that are the same, when compared and aligned for maximum correspondence over a comparison window, as measured using a sequence comparison algorithm or by manual alignment and visual inspection.

Both protein and nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988, *Proc. Natl. Acad. Sci. USA* 85(8):2444-2448; Altschul et al., 1990, *J. Mol. Biol.* 215(3): 403-410; Thompson et al., 1994, *Nucleic Acids Res.* 22(2): 4673-4680; Higgins et al., 1996, *Methods Enzymol.* 266:383-402; Altschul et al., 1990, *J. Mol. Biol.* 215(3):403-410; Altschul et al., 1993, *Nature Genetics* 3:266-272). Sequence comparisons are, typically, conducted using default parameters provided by the vendor or using those parameters set forth in the above-identified references, which are hereby incorporated by reference in their entireties.

As indicated supra, the subject invention provides methods of screening transgenic plants, plant cells or plant parts comprising growing a transformed plant, plant cell, or plant part containing the Atwbc19 or Atwbc16 polynucleotide sequence, or a fragment of the Atwbc19 or Atwbc16 polynucleotide sequence that encodes a functional fragment of the transporter polypeptide on kanamycin containing media; and identifying kanamycin resistant plants, plant cells, or plant parts. In one aspect of the screening invention, the screened plants, plant cells or plant parts are transformed with the Atwbc19 or Atwbc16 polynucleotide sequence or a functional fragment thereof in addition to a gene of interest. In a second aspect of the screening invention, the transformed plant, plant cell or plant part can be transformed with one or more genetic construct that does not contain the Atwbc19 or Atwbc16 polynucleotide sequence or a functional fragment thereof. In this second aspect of the invention the transformed plant, plant cell or plant part is transformed with a genetic construct that contains a gene of interest, however the construct does not contain a gene (e.g., neomycin phosphotransferase type II (nptII)) that confers kanamycin resistance upon the transformed plant, plant cell or plant part. Rather, the endogenous (naturally present) Atwbc19 or Atwbc16 polynucleotide sequence or a functional fragment thereof confers resistance to kanamycin on the transformed plant, plant cell or plant part. Thus, the second aspect of the screening method provides for the screening of a transgenic plant, plant cell or plant part that contains a heterologous gene of interest and an endogenous Atwbc19 or Atwbc16 polynucleotide sequence or a functional fragment thereof that occurs in the non-transformed plant, plant cell, or plant part.

The subject invention provides transformed plant cells, transgenic or transformed plant parts and transgenic plants which contain one or more genetic constructs, vectors, or expression cassettes comprising: polynucleotides encoding homologues (or functional fragments of said homologues) of the Atwbc19 or Atwbc16 polynucleotide sequence; the Atwbc19 or Atwbc16 polynucleotide sequence or biologically active fragments of the Atwbc19 or Atwbc16 polynucleotide sequence, operably linked to control elements. As used herein, the term "plant" includes algae and higher plants (including, but not limited to trees). Thus, algae, monocots, and dicots may be transformed with genetic constructs of the invention, expression cassettes, or vectors according to the invention. Specifically excluded from the subject invention are those non-genetically modified plants, plant parts or plant cells that contain the Atwbc19 or Atwbc16 polynucleotide sequence within the naturally occurring genome of the plant, plant part or plant cell. In certain embodiments, transformed plants, plant cells or plant parts where the transformed plant, plant cell or plant part contains, as a part of its endogenous (or naturally existing genetic content) the Atwbc19 or Atwbc16 polynucleotide sequence or a functional fragment thereof are excluded from the subject invention. Other embodiments provide transformed plants, plant parts and/or plant cells in which a heterologous promoter has been introduced into said transformed plants, plant parts and/or plant cells (via homologous recombination) such that it is operably linked to the endogenous Atwbc19 or Atwbc16 polynucleotide sequence or a functional fragment or equivalent thereof to direct expression of the Atwbc19 or Atwbc16 polynucleotide sequences (see, for example, Shaked et al. (2005) which is hereby incorporated by reference in its entirety). Yet other embodiments provide transformed plants, plant parts and/or plant cells in which a heterologous enhancer sequence has been introduced into said transformed plants, plant parts and/or plant cells (via homologous recombination) such that it is operably linked to the endogenous Atwbc19 or Atwbc16 polynucleotide sequence or a functional fragment or equivalent thereof to direct expression of the Atwbc19 or Atwbc16 polynucleotide sequences. Transgenic plants, plant parts or plant cells of the subject invention can contain additional selectable markers, such as neomycin phosphotransferase type II (nptII), in addition to homologues (or functional fragments of said homologues) of the Atwbc19 or Atwbc16 polynucleotide sequence; the Atwbc19 or Atwbc16 polynucleotide sequence or biologically active fragments of the Atwbc19 or Atwbc16 polynucleotide sequence.

Following transformation, a plant may be regenerated, e.g., from single cells, callus tissue or leaf discs, as is standard in the art. Almost any plant can be entirely regenerated from cells, tissues, and organs of the plant. Available techniques are reviewed in Vasil et al. (1984) in *Cell Culture and Somatic Cell Genetics of Plants, Vols. I, II, and III, Laboratory Procedures and Their Applications* (Academic press); and Weissbach et al. (1989) *Methods for Plant Mol. Biol.* The transformed plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited, and then seeds harvested to ensure expression of the desired phenotypic characteristic has been achieved. In the case of the subject invention, one of the desired phenotypic characteristics is kanamycin resistance that is conferred by the introduction of the Atwbc19 or Atwbc16 polynucleotide sequence (or a functional fragment thereof) into the plant, plant cell, or plant part.

The present invention also provides a plant comprising a plant cell as disclosed. Transformed seeds and plant parts are also encompassed. As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to naturally occurring, deliberate, or inadvertent caused mutations. Mutant progeny that have the same function or biological activity as screened for in the originally transformed cell are included. Thus, kanamycin resistance is one function of said mutant progeny. Where distinct designations are intended, it will be clear from the context.

In addition to a plant, the present invention provides any clone of such a plant, seed, or hybrid descendants, and any part of any of these, such as cuttings or seed. The invention provides any plant propagule, that is any part which may be used in reproduction or propagation, sexual or asexual, including cuttings, seed, and so on. Also encompassed by the invention is a plant which is a sexually or asexually propagated off-spring, clone, or descendant of such a plant; or any part or propagule of said plant, off-spring, clone, or descendant. Plant extracts and derivatives are also provided.

Exemplary plants in which the subject invention may be practiced include corn, maize, cotton, soybean, or canola. Thus, the subject invention provides transgenic or transformed kanamycin resistant corn, maize, cotton, soybean, or canola plants, plant parts, or plant cells which contain the Atwbc19 or Atwbc16 polynucleotide sequence or a functional fragment thereof. In certain embodiments, the subject invention provides transgenic or transformed aminoglycoside resistant corn, maize, cotton, soybean, or canola plants, plant parts, or plant cells which contain the Atwbc19 or Atwbc16 polynucleotide sequence or a functional fragment thereof. In other embodiments, transgenic or transformed kanamycin resistant corn, maize, cotton, soybean, or canola plants, plant parts, or plant cells which contain homologues (or functional fragments of said homologues) of the Atwbc19 or Atwbc16 polynucleotide sequence; the Atwbc19 or Atwbc16 polynucleotide sequence or biologically active fragments of the Atwbc19 or Atwbc16 polynucleotide sequence are provided.

Also according to the invention, there is provided a plant cell having the constructs of the invention. A further aspect of the present invention provides a method of making such a plant cell involving introduction of a vector including the construct into a plant cell. For integration of the construct into the plant genome, such introduction will be followed by recombination between the vector and the plant cell genome to introduce the sequence of nucleotides into the genome. RNA encoded by the introduced nucleic acid construct may then be transcribed in the cell and descendants thereof, including cells in plants regenerated from transformed material. A gene stably incorporated into the genome of a plant is passed from generation to generation to descendants of the plant, so such descendants should show the desired phenotype.

The present invention also provides a plant comprising a plant cell as disclosed. Transformed seeds and plant parts are also encompassed. As used herein, the expressions "cell", "cell line", and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to naturally occurring, deliberate, or inadvertently caused mutations. Mutant progeny that have the same function or biological activity as screened for in the originally transformed cell are included. Where distinct designations are intended, it will be clear from the context.

In addition to a plant, the present invention provides any clone of such a plant, seed, or hybrid descendants, and any part of any of these, such as cuttings or seed. The invention provides any plant propagule, that is any part which may be used in reproduction or propagation, sexual or asexual, including cuttings, seed, and so on. Also encompassed by the invention is a plant which is a sexually or asexually propagated off-spring, clone, or descendant of such a plant; or any part or propagule of said plant, off-spring, clone, or descendant. Plant extracts and derivatives are also provided.

As is apparent to the routineer in this technology, the disclosed methods allow for the expression of a gene of interest in any plant. The invention thus relates generally to methods for the production of transgenic plants (both monocots and dicots). As used herein, the term "transgenic plants" refers to plants (algae, monocots, or dicots), comprising plant cells in which homologous or heterologous polynucleotides are expressed as the result of manipulation by the hand of man.

"Nucleotide sequence", "polynucleotide" or "nucleic acid" can be used interchangeably and are understood to mean, according to the present invention, either a double-stranded DNA, a single-stranded DNA or products of transcription of the said DNAs (e.g., RNA molecules). It should also be understood that the present invention does not relate to genomic polynucleotide sequences in their natural environment or natural state. The nucleic acid, polynucleotide, or nucleotide sequences of the invention can be isolated, purified (or partially purified), by separation methods including, but not limited to, ion-exchange chromatography, molecular size exclusion chromatography, or by genetic engineering methods such as amplification, subtractive hybridization, cloning, subcloning or chemical synthesis, or combinations of these genetic engineering methods.

The subject invention also provides genetic constructs comprising: a) a polynucleotide sequence encoding the Atwbc19 or Atwbc16 polypeptide sequence or a functional fragment thereof. Genetic constructs of the subject invention can also contain one or more of the following additional elements: regulatory elements such as promoters, termination sequences or enhancers; additional selectable markers; or other structural genes that are used to form a transformed plant, plant cell, or plant part.

Also within the scope of the subject instant invention are vectors or expression cassettes containing polynucleotides encoding the Atwbc19 or Atwbc16 polypeptide sequence, or a functional fragment thereof, operably linked to regulatory elements. The vectors and expression cassettes may contain additional transcriptional control sequences as well. The vectors and expression cassettes may further comprise selectable markers and/or structural genes (e.g., insecticidal proteins). The expression cassette may contain at least one additional gene, operably linked to control elements, to be co-transformed into the plant, plant cell, or plant part. Alternatively, the additional gene(s) and control element(s) can be provided on multiple expression cassettes. Such expression cassettes are provided with a plurality of restriction sites for insertion of the Atwbc19 or Atwbc16 polynucleotide sequence or a functional fragment thereof that are to be under the transcriptional regulation of the regulatory regions. The expression cassette(s) may additionally contain other selectable marker genes operably linked to control elements.

The expression cassette will include in the 5'-3' direction of transcription, a transcriptional and translational initiation region, a DNA sequence of the invention, and a transcriptional and translational termination region functional in plants. The transcriptional initiation region, the promoter, may be native or analogous, or foreign or heterologous, to the host cell. Additionally, the promoter may be the natural sequence or alternatively a synthetic sequence. By "foreign" is intended that the transcriptional initiation region is not found in the plant into which the transcriptional initiation region is introduced.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144;

Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the polynucleotides encoding the Atwbc19 or Atwbc16 polypeptides set forth supra can be optimized for expression in the transformed. That is, the genes can be synthesized using species-preferred codons corresponding to the species of interest. Methods are available in the art for synthesizing for example, plant-preferred genes. See, for example, U.S. Pat. Nos. 5,380,831 and 5,436,391, and Murray et al. (1989) *Nucleic Acids Res.* 17:477-498, herein incorporated by reference.

The expression cassettes may additionally contain 5' leader sequences in the expression cassette construct. Translation leaders are known in the art and include: picornavirus leaders, for example, EMCV leader (Encephalomyocarditis 5' non-coding region), Elroy-Stein et al. (1989) *PNAS USA* 86:6126-6130; potyvirus leaders, for example, TEV leader (Tobacco Etch Virus), Allison et al. (1986); MDMV Leader (Maize Dwarf Mosaic Virus), *Virology* 154:9-20; human immunoglobulin heavy-chain binding protein (BiP), Macejak et al. (1991) *Nature* 353:90-94; untranslated leader from the coat protein mRNA of alfalfa mosaic virus (AMV RNA 4), Jobling et al. (1987) *Nature* 325:622-625; tobacco mosaic virus leader (TMV), Gallie et al. (1989) in *Molecular Biology of RNA*, ed. Cech (Liss, N.Y.), pp. 237-256; and maize chlorotic mottle virus leader (MCMV), Lommel et al. (1991) *Virology* 81:382-385. See also, Della-Cioppa et al. (1987) *Plant Physiol.* 84:965-968. Other methods known to enhance translation can also be utilized.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, base substitutions, e.g., transitions and transversions, may be involved. A number of promoters can be used in the practice of the invention. The promoters can be selected based on the desired outcome. Strong promoters may be used to produce high levels of gene transcription. Alternatively, inducible promoters may be used to selectively active gene transcription when the appropriate signal is provided. Constitutive promoters may be utilized to continuously drive gene transcription. Tissue specific promoters may also be used in the practice of the invention in order to provide localized production of gene transcripts in a desired tissue. Developmental promoters may, likewise, be used to drive transcription of a gene during a particular developmental stage of the plant. Thus, a gene of interest can be combined with constitutive, tissue-specific, inducible, developmental, or other promoters for expression in plants depending upon the desired outcome.

Constitutive promoters include, for example, CaMV 35S promoter (Odell et al. (1985) *Nature* 313:810-812; rice actin (McElroy et al. (1990) *Plant Cell* 2:163-171; ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include those in U.S. Pat. Nos. 5,608,149; 5,608,144; 5,604,121; 5,569,597; 5,466,785; 5,399,680; 5,268,463; and 5,608,142. Each of the aforementioned patents and references is hereby incorporated by reference in its entirety.

A number of inducible promoters are known in the art. For example, a pathogen-inducible promoter can be utilized. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116; Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386; Cordero et al. (1992) *Physiol. Mol. Plant Path.* 41:189-200; each of which is incorporated by reference in its entirety.

Wound-inducible promoters may be used in the genetic constructs of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498; wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323: 73-76); MPI gene (Corderok et al. (1994) *Plant J.* 6(2):141-150; and the like. These references are also incorporated by reference in their entireties.

Chemical-regulated promoters can be used to modulate the expression of a gene in a plant through the application of an exogenous chemical regulator. Depending upon the objective, the promoter may be a chemical-inducible promoter, where application of the chemical induces gene expression; or a chemical-repressible promoter, where application of the chemical represses gene expression. Chemical-inducible promoters are known in the art and include, but are not limited to, the maize In2-2 promoter, which is activated by benzene sulfonamide herbicide safeners; the maize GST promoter, which is activated by hydrophobic electrophilic compounds that are used as pre-emergent herbicides; and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci USA* 88:10421-10425 and McNellis et al. (1998) *Plant J.* 14(2):247-257), and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue specific promoters can also be used in the practice of the subject invention. For example, leaf-specific promoters can similarly be used if desired, and are taught in references which include Yamamoto et al. (1997) *Plant J.* 12(2):255-265; Kawamata et al. (1997) *Plant Cell Physiol.* 38(7):792-803; Hansen et al. (1997) *Mol. Gen. Genet.* 254(3):337-343; Russel et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5)773-778; Lam (1994) *Results Probl. Cell Differ.* 20:181-196; Orozco et al. (1993) *Plant*

Mol. Biol. 23(6):1129-1138; Matsuoka et al. (1993) Proc. Natl. Acad. Sci USA:90(20) 9586-9590; and Guevara-Garcia et al. (1993) Plant J. 4(3):495-505. Alternatively, root-specific promoters are known and can be selected from the many available from the literature. See, for example, Hire et al. (1992) Plant Mol. Biol. 20(2):207-218 (soybean root-specific glutamine synthetase gene); Keller and Baumgartner (1991) Plant Cell 3(10):1051-1061 (root-specific control element in the GRP 1.8 gene of French bean); Sanger et al. (1990) Plant Mol. Biol. 14(3):433-443 (root-specific promoter of the mannopine synthase (MAS) gene of Agrobacterium tumefaciens) Miao et al. (1991) Plant Cell 3(1):11-22 (full-length cDNA clone encoding cytosolic glutamine synthetase (GS), which is expressed in roots and root nodules of soybean). Bogusz et al. (1990) Plant Cell 2(7):633-641 (root specific promoters from hemoglobin genes from the nitrogen-fixing nonlegume Parasponia andersonii and the related non-nitrogen-fixing nonlegume Trema tomeniosa; Leach and Aoyagi (1991) Plant Science (Limerick) 79(1):69-76 (rolC and rolD root-including genes of Agrobacterium rhizogenes); Teeri et al. (1989) EMBO J. 8(2):343-350 (octopine synthase and TR2' gene); (VfENOD-GRP3 gene promoter); Kuster et al. (1995) Plant Mol. Biol. 29(4):759-772 and Capana et al. (1994) Plant Mol Biol. 25(4):681-691 (rolB promoter). See also U.S. Pat. Nos. 5,837,876; 5,750,386; 5,633,363; 5,459,252; 5,401,836; 5,110,732; and 5,023,179.

Other tissue specific promoters can also be used in the practice of the subject invention (see, for example U.S. Pat. No. 6,544,783). For example, xylem/vascular/tracheid-specific promoters, such as those disclosed in Milioni et al. (2002) Plant Cell, 14:2813-2824; Zhong et al. (1999) Plant Cell, 11:2139-2152; Ito et al. (2002) Plant Cell, 14:3201-3211; Parker et al. (2003) Development 130:2139-2148; Bourquin et al. (2002) Plant Cell 14:3073-3088 (each of which is hereby incorporated by reference in its entirety) can be used in the practice of the subject invention.

"Seed-preferred" promoters include both "seed-specific" promoters (those promoters active during seed development such as promoters of seed storage proteins) as well as "seed-germinating" promoters (those promoters active during seed germination). See Thompson et al. (1989) Bioassays 10:108, herein incorporated by reference. Such seed-preferred promoters include, but are not limited to, Cim1 (cytokinin-induced message); cZ10B1 (Maize 19 kDa zein); celA (cellulose synthase); gama-zein; Glob-1; bean β-phaseolin; napin; β-conglycinin; soybean lectin; cruciferin; maize 15 kDa zein; 22 kDa zein; 27 kDa zein; g-zein; waxy; shrunken 1; shrunken 2; globulin 1; etc.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

As used herein, the term "expression cassette" refers to a molecule comprising at least one coding sequence operably linked to a control sequence which includes all nucleotide sequences required for the transcription of cloned copies of the coding sequence and the translation of the mRNAs in an appropriate host cell. Such expression cassettes can be used to express eukaryotic genes in a variety of hosts such as bacteria, green algae, cyanobacteria, plant cells, fungal cells, yeast cells, insect cells and animal cells. As described herein, expression cassettes can include, but are not limited to, cloning vectors, specifically designed plasmids, viruses or virus particles. The cassettes may further include an origin of replication for autonomous replication in host cells, selectable markers, various restriction sites, a potential for high copy number and strong promoters.

By "vector" is meant any genetic element, such as a plasmid, phage, transposon, cosmid, chromosome, virus etc., which is capable of replication when associated with the proper control elements and which can transfer gene sequences between cells. Thus, the term includes cloning and expression vehicles, as well as viral vectors.

During the preparation of the constructs, the various fragments of DNA will often be cloned in an appropriate cloning vector, which allows for amplification of the DNA, modification of the DNA or manipulation of the DNA by joining or removing sequences, linkers, or the like. Preferably, the vectors will be capable of replication to at least a relatively high copy number in E. coli. A number of vectors are readily available for cloning, including such vectors as pBR322, vectors of the pUC series, the M13 series vectors, and pBluescript vectors (Stratagene; La Jolla, Calif.).

In order to provide a means of selecting transformed plants, plant parts or plant cells, the vectors for transformation can contain, in addition to the Awtbc19 polynucleotide sequence, or functional fragment thereof, another selectable marker gene. Marker genes are expressible DNA sequences which express a polypeptide which resists a natural inhibition by, attenuates, or inactivates a selective substance. Examples of such substances include antibiotics and, in the case of plant cells, herbicides. Selectable markers for use in animal, bacterial, plant, fungal, yeast, and insect cells are well known in the art. Exemplary selectable markers include bacterial transposons Tn5 or Tn 601(903) conferring resistance to aminoglycosides (selection for Geneticin-resistance (G418R), mycophenolic acid resistance (MPAR) (utilizing E. coli guanosine phosphoribosyl transferase (gpt) encoding the enzyme XGPRT; selection is performed on medium containing MPA and xanthin), methotrexate resistance (MTXR), or cadmium-resistance which incorporates the mouse metallotheionein gene (as cDNA cassette) on the vector which detoxifies heavy metal ions by chelating them.

Alternatively, a marker gene may provide some visible indication of cell transformation. For example, it may cause a distinctive appearance or growth pattern relative to plants or plant cells not expressing the selectable marker gene in the presence of some substance, either as applied directly to the plant or plant cells or as present in the plant or plant cell growth media. The use of such a marker for identification of plant cells containing a plastid construct has been described (Svab et al., 1993, supra). Numerous additional promoter regions may also be used to drive expression of the selectable marker gene, including various plant promoters and bacterial promoters which have been shown to function in plants.

A number of other markers have been developed for use with plant cells, such as resistance to chloramphenicol, the aminoglycoside G418, hygromycin, or the like. Other genes which encode a product involved in chloroplast metabolism may also be used as selectable markers. For example, genes which provide resistance to plant herbicides such as glyphosate, bromoxynil or imidazolinone may find particular use. Such genes have been reported (Stalker et al. (1985) J. Biol. Chem. 260:4724-4728 (glyphosate resistant EPSP); Stalker et al. (1985) J. Biol. Chem. 263:6310-6314 (bromoxynil resistant nitrilase gene); and Sathasivan et al. (1990) Nucl. Acids Res. 18:2188 (AHAS imidazolinone resistance gene)).

Methods of transforming cells with genetic constructs, vectors, or expression cassettes comprising the novel polynucleotides of the invention are also provided. These methods comprise transforming a plant or plant cell with a polynucleotide according to the subject invention. Plants and plant cells may be transformed by electroporation, *Agrobacterium* transformation (including vacuum infiltration), engineered plant virus replicons, electrophoresis, microinjection, micro-projectile bombardment, vacuum infiltration of *Agrobacterium*, micro-LASER beam-induced perforation of cell wall, or simply by incubation with or without polyethylene glycol (PEG). Plants transformed with a genetic construct of the invention may be produced by standard techniques known in the art for the genetic manipulation of plants. DNA can be transformed into plant cells using any suitable technology, such as a disarmed Ti-plasmid vector carried by *Agrobacterium* exploiting its natural gene transferability (EP-A-270355; EP-A-0116718; *NAR* 12(22):87211-87215 (1984); Townsend et al, U.S. Pat. No. 5,563,055); particle or microprojectile bombardment (U.S. Pat. No. 5,100,792; EP-A-444882; EP-A-434616; Sanford et al. U.S. Pat. No. 4,945,050; Tomes et al. (1995) "Direct DNA Transfer Into Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923-926); microinjection (WO 92/09696; WO 94/00583; EP 331083; EP 175966; Green et al. (1987) *Plant Tissue and Cell Culture*, Academic Press; Crossway et al. (1986) *Biotechniques* 4:320-334); electroporation (EP 290395; WO 8706614; Riggs et al. (1986) *Proc. Nat. Acad. Sci. USA* 83:5602-5606; D'Halluin (1992) *Plant Cell* 4:1495-1505); other forms of direct DNA uptake (DE 4005152; WO 9012096; U.S. Pat. No. 4,684,611; Paszkowski et al. (1984) *EMBO J.* 3:2717-2722); liposome-mediated DNA uptake (e.g., Freeman et al. (1984) *Plant Cell Physiol.* 29:1353); or the vortexing method (e.g., Kindle (1990) *Proc. Nat. Acad. Sci USA* 87:1228). Physical methods for the transformation of plant cells are reviewed in Oard (1991) *Biotech. Adv.* 9:1-11. See generally, Weissinger et al. (1988) *Ann. Rev. Genet.* 22:421-477; Sanford et al. (1987) *Particulate Science and Technology* 5:27-37; Christou et al. (1988) *Plant Physiol.* 87:671-674; McCabe et al. (1988) *Bio/Technology* 6:923-926; Finer and McMullen (1991) *In Vitro Cell Dev. Biol.* 27P:175-182; Singh et al. (1998) *Theor. Appl. Genet.* 96:319324; Datta et al. (1990) *Biotechnology* 8:736-740; Klein et al. (1988) *Pro. Natl. Acad. Sci. USA* 85:4305-4309; Klein et al. (1988) *Biotechnology* 6:559-563; Tomes, U.S. Pat. No. 5,240,855; Buising et al., U.S. Pat. Nos. 5,322,783 and 5,324,646; Klein et al. (1988) *Plant Physiol.* 91:440-444; Fromm et al. (1990) *Biotechnology* 8:833-839; Hooykaas-Van Slogteren et al. (1984) *Nature* (London) 311:763-764; Bytebier et al (1987) *Proc. Natl. Acad. Sci. USA* 84:5345-5349; De Wet et al. (1985) in *The Experimental Manipulation of Ovule Tissues*, ed. Chapman et al. (Longman, N.Y.), pp. 197-209; Kaeppler et al. (1990) *Plant Cell Reports* 9:415-418 and Kaeppler et al. (1992) *Theor. Appl. Genet.* 84:560-566; Li et al. (1993) *Plant Cell Reports* 12:250-255; Christou and Ford (1995) *Annals of Botany* 75:407-413; and Osjoda et al. (1996) *Nature Biotechnology* 14:745-750; U.S. Pat. No. 5,661,017; PCT/US00/10103 (WO 00/62601); all of which are herein incorporated by reference in their entireties.

*Agrobacterium* transformation is used by those skilled in the art to transform algae and dicotyledonous species. Substantial progress has been made towards the routine production of stable, fertile transgenic plants in almost all economically relevant monocot plants (Toriyama et al. (1988) *Bio/Technology* 6:1072-1074; Zhang et al. (1988) *Plant Cell Rep.* 7:379-384; Zhang et al. (1988) *Theor. Appl. Genet.* 76:835-840; Shimamoto et al. (1989) *Nature* 338:274-276; Datta et al. (1990) *Bio/Technology* 8:736-740; Christou et al. (1991) *Biotechnology* 9:957-962; Peng et al. (1991) International Rice Research Institute, Manila, Philippines, pp. 563-574; Cao et al. (1992) *Plant Cell Rep.* 11:585-591; Li et al. (1993) *Plant Cell Rep.* 12:250-255; Rathore et al. (1993) *Plant Mol. Biol.* 21:871-884; Fromm et al. (1990) *Bio/Technology* 8:833-839; Gordon-Kamm et al. (1990) *Plant Cell* 2:603-618; D'Halluin et al. (1992) *Plant Cell* 4:1495-1505; Walters et al. (1992) *Plant Mol. Biol.* 18:189-200; Koziel et al. (1993) *Biotechnology* 11:194-200; Vasil, I. K. (1994) *Plant Mol. Biol.* 25:925-937; Weeks et al. (1993) *Plant Physiol.* 102: 1077-1084; Somers et al. (1992) *Bio/Technology* 10:1589-1594; WO 92/14828). In particular, *Agrobacterium* mediated transformation is now emerging also as a highly efficient transformation method in monocots (Hiei et al. (1994) *The Plant Journal* 6:271-282). See also, Shimamoto, K. (1994) *Current Opinion in Biotechnology* 5:158-162; Vasil et al. (1992) *Bio/Technology* 10:667-674; Vain et al. (1995) *Biotechnology Advances* 13(4):653-671; Vasil et al. (1996) *Nature Biotechnology* 14:702.

Microprojectile bombardment, electroporation, and direct DNA uptake are preferred where *Agrobacterium* is inefficient or ineffective. Alternatively, a combination of different techniques may be employed to enhance the efficiency of the transformation process, e.g., bombardment with *Agrobacterium*-coated microparticles (EP-A-486234) or microprojectile bombardment to induce wounding followed by co-cultivation with *Agrobacterium* (EP-A-486233).

The particular choice of a transformation technology will be determined by its efficiency to transform certain plant species as well as the experience and preference of the person practicing the invention with a particular methodology of choice. It will be apparent to the skilled person that the particular choice of a transformation system to introduce nucleic acid into plant cells is not essential to or a limitation of the invention, nor is the choice of technique for plant regeneration.

As is apparent to one of ordinary skill in the art, the peptides encoded by the disclosed herein may be encoded by multiple polynucleotide sequences because of the redundancy of the genetic code. It is well within the skill of a person trained in the art to create these alternative DNA sequences encoding the same, or essentially the same, amino acid sequences. These variant DNA sequences are within the scope of the subject invention. One skilled in the art would also recognize that any polynucleotide which is transcribed, processed, and translated the amino acid sequence of SEQ ID NO: 2 is within the scope of the invention and can be used for the transformation of a plant, plant cell or plant part.

Another aspect of the invention provides vectors for the cloning and/or the expression of the Atwbc19 or Atwbc16 gene, or functional fragment thereof, in prokaryotic or animal cells. The subject invention also provides methods of inducing kanamycin resistance into prokaryotic or animal cells. As indicated supra, one aspect of the invention a method of imparting kanamycin resistance to a prokaryotic or animal cell susceptible to kanamycin comprising:

a) obtaining an animal or prokaryotic cell that is susceptible or sensitive to kanamycin; and b) transforming said animal or prokaryotic cell with Atwbc19 or Atwbc16, or a fragment of the Atwbc19 or Atwbc16 gene that encodes a functional fragment of the transporter polypeptide.

Again, the phrases "functional fragment", "biologically active fragment" or "active fragment" can be used interchangeably. Further, these phrases are defined, in the context of this invention, as providing the ability to confer kanamycin resistance in prokaryotes or animal cells that are not resistant to kanamycin in their naturally occurring form (i.e., a non-transformed animal or prokaryotic cell).

The invention also encompasses the host cells transformed by a vector according to the invention. These cells may be obtained by introducing into host cells a nucleotide sequence inserted into a vector as defined above, and then culturing the said cells under conditions allowing the replication and/or the expression of the polynucleotide sequences of the subject invention. The invention also encompasses the host cells transformed by a vector according to the invention. These cells may be obtained by introducing into host cells a nucleotide sequence inserted into a vector as defined above, and then culturing the said cells under conditions allowing the replication and/or the expression of the polynucleotide sequences of the subject invention. For the purposes of this invention, the phrases "host cell" and "host cells" are defined as prokaryotic or animal cells.

The host cell may be chosen from eukaryotic or prokaryotic systems, such as for example bacterial cells, (Gram negative or Gram positive), yeast cells (for example, *Saccharomyces cereviseae* or *Pichia pastoris*), animal cells (such as Chinese hamster ovary (CHO) cells), and/or insect cells using baculovirus vectors. In some embodiments, the host cells for expression of the polypeptides include, and are not limited to, those taught in U.S. Pat. Nos. 6,319,691, 6,277,375, 5,643,570, or 5,565,335, each of which is incorporated by reference in its entirety, including all references cited within each respective patent.

As discussed supra, vectors used to transform a host cell can contain additional elements. These elements include, and are not limited to, regulatory elements such as promoters, termination sequences or enhancers; additional selectable markers; or other structural genes that are used to form a transformed host cell.

Furthermore, a host cell may be chosen which modulates the expression of the inserted sequences, or modifies and processes the gene product in the specific fashion desired. Expression from certain promoters can be elevated in the presence of certain inducers; thus, expression of the genetically engineered polypeptide may be controlled. Furthermore, different host cells have characteristic and specific mechanisms for the translational and post-translational processing and modification (e.g., glycosylation, phosphorylation) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can also to provide glycosylation of a protein.

The terms "purified" and "isolated", when referring to a polynucleotide, nucleotide, or nucleic acid, indicate a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecules but is not flanked by both of the coding or noncoding sequences that flank that part of the molecule in the genome of the organism in which it naturally occurs (e.g., DNA excised with a restriction enzyme); (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transfected cells, and (iii) cell clones, e.g., as these occur in a DNA library such as a cDNA or genomic DNA library.

The term "polynucleotide" as used herein refers to a polymeric form of nucleotides of any length, either ribonucleotides or deoxyribonucleotides. This term refers only to the primary structure of the molecule and thus includes double- and single-stranded DNA and RNA. It also includes known types of modifications, for example, labels which are known in the art, methylation, "caps", substitution of one or more of the naturally occurring nucleotides with an analog, internucleotide modifications, such as those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide.

"Control elements" include both "transcriptional control elements" and "translational control elements". "Transcriptional control elements" include "promoter", "enhancer", and "transcription termination" elements. Promoters and enhancers consist of short arrays of DNA sequences that interact specifically with cellular proteins involved in transcription (Maniatis et al. (1987) *Science* 236:1237). Promoter and enhancer elements have been isolated from a variety of eukaryotic sources including genes in plants, yeast, insect and mammalian cells and viruses (analogous control elements, i.e., promoters, are also found in prokaryotes). The selection of a particular promoter and enhancer depends on what cell type is to be used to express the peptide of interest. Some eukaryotic promoters and enhancers have a broad host range while others are functional in a limited subset of cell types (for review see Voss et al. (1986) *Trends Biochem. Sci.* 11:287 and Maniatis et al. (1987) supra). Transcriptional control elements suitable for use in plants are well known in the art. "Translational control, elements" include translational initiation regions and translational termination regions functional in plants.

All publications, patents and patent applications cited herein, whether supra or infra, are hereby incorporated by reference in their entirety to the extent that the reference is not inconsistent with the teachings provided herein. As used in this specification and the appended claims, the singular forms "a," "an" and "the" include plural references unless the context clearly dictates otherwise and the terms "comprising", consisting essentially of" and "consisting of" can be substituted each for the other.

EXAMPLE 1

Figure 5:
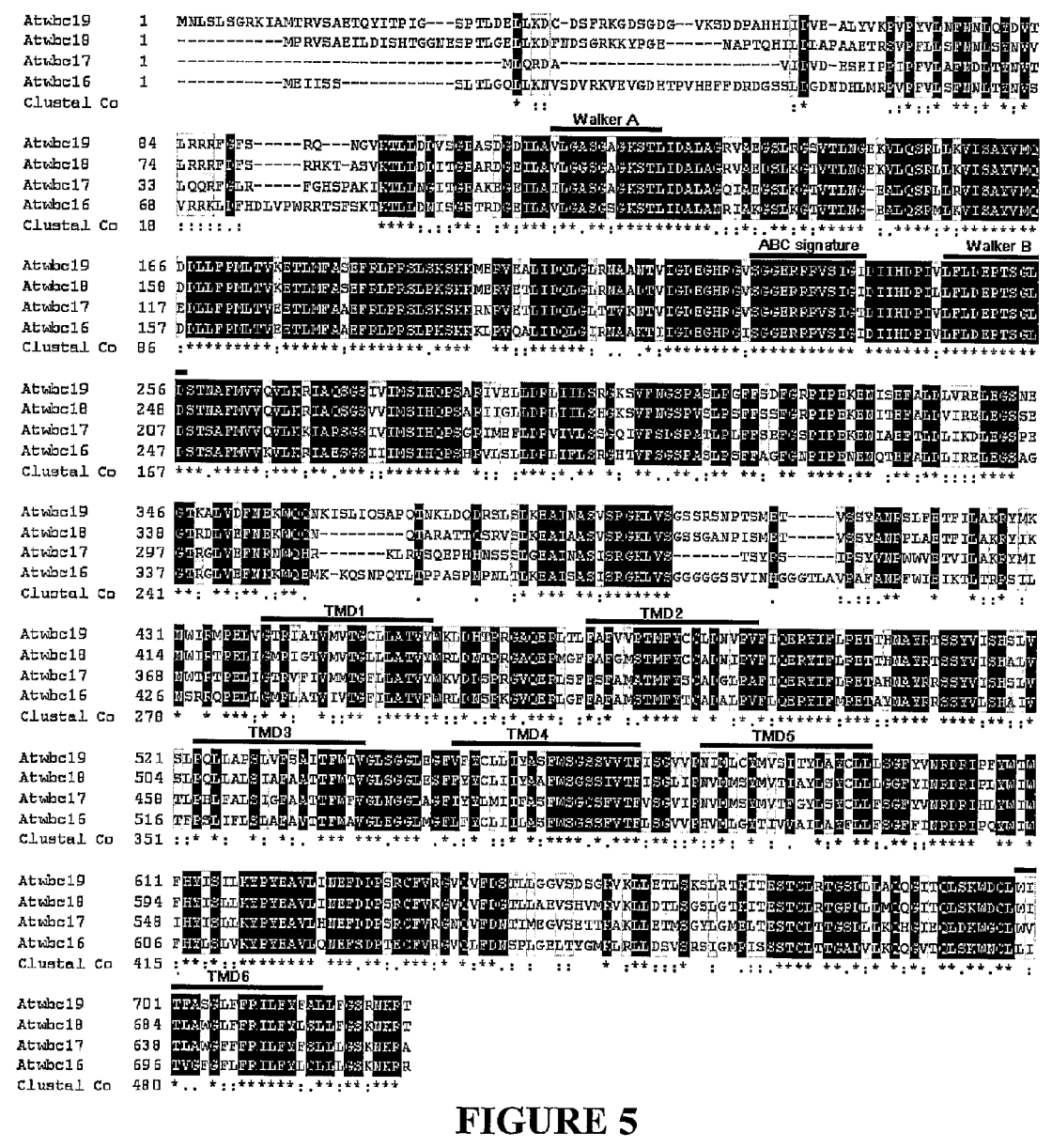

In a previous study in which we examined the genome-wide response of *Arabidopsis* to the xenobiotic compound trinitrotoluene (TNT) via cDNA microarrays, we found that Atwbc19 (At3g55130) was among upregulated genes (Mentewab et al., 2005). Given the role of ABC transporters in cellular detoxification we sought to further characterize this gene. Initial surreptitious characterization of mutants revealed that root growth of Atwbc19 knockout mutants on media containing kanamycin was much slower than that of other ABC mutants. We specifically compared the kanamycin resistance level of mutants of Atwbc19 (SALK__107731) and two close homologues Atwbc18 (SALK__100187) and Atwbc16 (SALK__119868) sharing over 76% peptide similarity with Atwbc19 (FIG. 5).

germinated on MSO media for 2 weeks, with 2 replicate samples per line. An ELISA was performed using a kit according to the manufactures instructions (Agdia, Elkhart, Ind., USA).

TABLE 1

Primers used for PCR characterization of insertional mutants.

| Gene | Loci | Mutant | Forward reverse primers | Product size |
| --- | --- | --- | --- | --- |
| Atwbc19 | At3g55130 | SALK_107731 | GACGAAACTCGGAAGCGAACA GGTGCAGAGCAGAAGCCAAAA | 937 |
| Atwbc18 | At3g55110 | SALK_100187 | GGTCCTGTTCTCAAGCATGTGG AAGAAGCCATCGCTGCAAGTG | 895 |
| Atwbc16 | At3g55090 | SALK_119868 | AAAGCGATTCATAGGTGCTTTTG CTACACTTGCGCCGATGCTCT | 922 |
| T-DNA | LBb1 | | GCGTGGACCGCTTGCTGCAACT | |

Figure 6A:
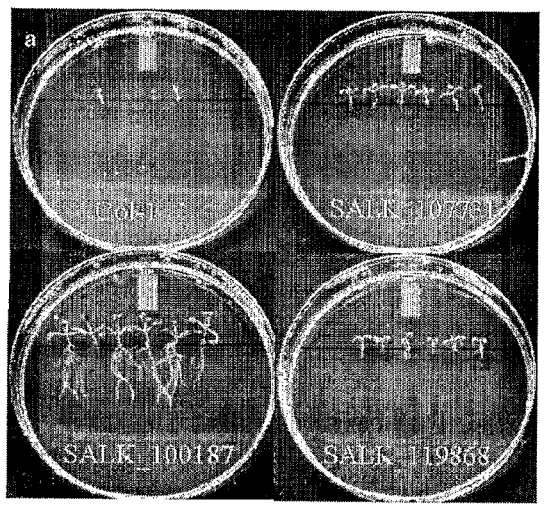
FIGS. 6A-B. Root growth and NPTII synthesis levels in control *Arabidopsis thaliana* Col1 and homozygous insertional knockout mutants Atwbc19 (SALK_107731), Atwbc16 (SALK_119868) and Atwbc18 (SALK_100187).
Figure 6B:
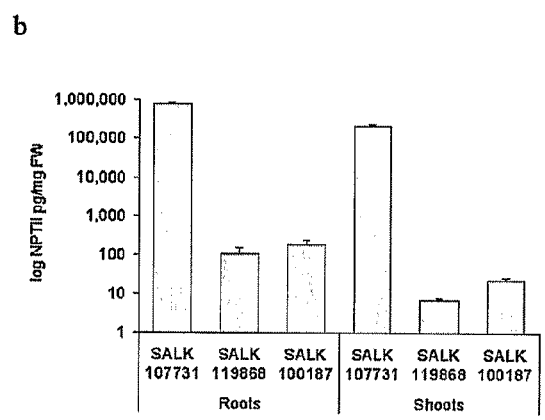

The mutants are T-DNA insertional mutants transformed with plasmid pROK2[2] containing an nptII gene, under the control of the nopaline synthase (nos) promoter. Therefore, we also compared their NPTII protein synthesis levels by ELISA assays. On media without kanamycin, there was no significant difference in root growth between the 3 lines. On media with kanamycin, root growth of line SALK__107731 was not different than that of SALK__119868 (0.31±0.04 and 0.30±0.03 cm, respectively) and clearly less than that of SALK__100187 (1.82±0.25 cm) as illustrated in FIG. 6. However, the amount of NPTII protein synthesized was more than 1000-fold in the SALK__107731 mutant compared to the other two mutants. Thus, these results suggested that Atwbc19 had a role in kanamycin resistance while its two close homologues did not. The estimated level of resistance conferred by Atwbc19, under the control of its native promoter is equivalent to 1 µg NPTII per mg fresh weight, an expression level conferred by the nos promoter. It also implied that Atwbc19 could be used as a kanamycin selection marker to generate transgenic plants instead of using the nptII gene. The interest in using Atwbc19 as a selection marker was two-fold. First, the transgenic plants would be valuable to confirm the role of Atwbc19 without the confounding effect of the nptII gene. Second, is the novelty and usefulness of Atwbc19 as an antibiotic selectable marker.

Characterization of Insertional Mutants

Sequence-tagged insertional mutant lines for the three ABC transporters, Atwbc19 (SALK__107731), Atwbc18 (SALK__100187) and Atwbc16 (SALK__119868) were obtained from ABRC *Arabidopsis* knock-out library. Homozygosity was tested by PCR of genomic DNA using 3 primers (Table 1). Two of the primers are specific to the native gene and amplify a known fragment. The third primer is specific to the T-DNA. Where the T-DNA is inserted between the two gene specific primers, a smaller fragment is generated allowing the identification of insertion in the gene of interest. The fragment was sequenced to ensure that it mapped at the expected loci. Kanamycin resistance was assessed by growing the mutants on MSO media with and without 100 mg/l kanamycin. Stratified seeds were germinated on 4 Petri dishes with 6 plants for each line and placed vertically in a growth chamber at 25 degrees. Root length was measured after 2 weeks. To quantify NPTII protein levels, total protein was extracted from 100 mg of root and shoot tissue from seedlings

EXAMPLE 2

During characterization of Atwbc19 knockout mutants we observed that root growth on media containing kanamycin was much slower than that of other mutants. We compared tobacco transformation (Horsch et al., 1985) efficiencies among three plasmids containing overexpressed Atwbc19, nptII, and both genes together (FIG. 1A). Transgenic plants were recovered from each construct using selection of 50, 100 and 200 mg/l kanamycin, but the transformation efficiency differed among treatments. A selection regime of 50 mg/l kanamycin resulted in less than 8% efficiency for any of the three plasmids, indicating that the selection pressure was not sufficient (FIG. 1B). Using Atwbc19 alone as the selection gene, the majority of plants recovered media containing 100 or 200 mg/l kanamycin were transgenic (73 and 69% respectively). However, selection at 200 mg/l kanamycin was overall less effective since the total number of transgenic plants regenerated was decreased from 40% to 19% per explant. Thus, it appears that 100 mg/l kanamycin is the most appropriate selection regime for tobacco using the ABC transporter under the control of the 35S promoter, in which its efficiency is comparable to that of nptII driven by the double 35S promoter with a selection regime of 200 mg/l kanamycin. When both cassettes were present, the transformation efficiency was significantly higher than either of them separately.

We confirmed that Atwbc19 was stably integrated in transgenic plants via Southern blot analysis, in which all histochemically stained GUS-positive plants showed presence of the Atwbc19 gene at the expected size (FIG. 1C). Additionally, all transgenic plants appeared morphologically normal and fertile. No deleterious or pleiotropic effects of the transgene were observed.

To further characterize Atwbc19-only transgenic plants, segregation analysis was performed by plating $T_1$ seeds on media containing 200 mg/l kanamycin (FIG. 2A). Lines segregating 3:1 were selected for northern blot analysis to examine patterns of Atwbc19 transcription. Expression of Atwbc19 was confirmed (FIG. 2B) and 2 transgenic events, 28 and 30, were selected for root growth assays. ELISA demonstrated that plants from both events contained no NPTII. As expected, transgenic lines showed a highly significant increase in kanamycin resistance compared to non-transgenic tobacco (t-test, P<0.001). Root length for control tobacco was 0.37±0.09 cm; 1.03±0.55 cm for #28 and 2.02±1.16 cm for #30 on media with 200 mg/l kanamycin. Because the experiment was conducted on segregating $T_1$ seeds, we observed a clear difference between transgenic and non-transgenic seedlings (FIG. 2C). The non-transgenic segregants were bleached and stunted, which are characteristic of kanamycin sensitivity. The segregation was also clear when we examined the root length distribution frequency. A bimodal distribution was observed for the transgenic lines (see FIG. 7). Plants from these two transgenic events displayed no resistance to related aminoglycosides (amikacin, geneticin, gentamycin, streptomycin, hygromycin) and chloramphenicol.

Figure 4:
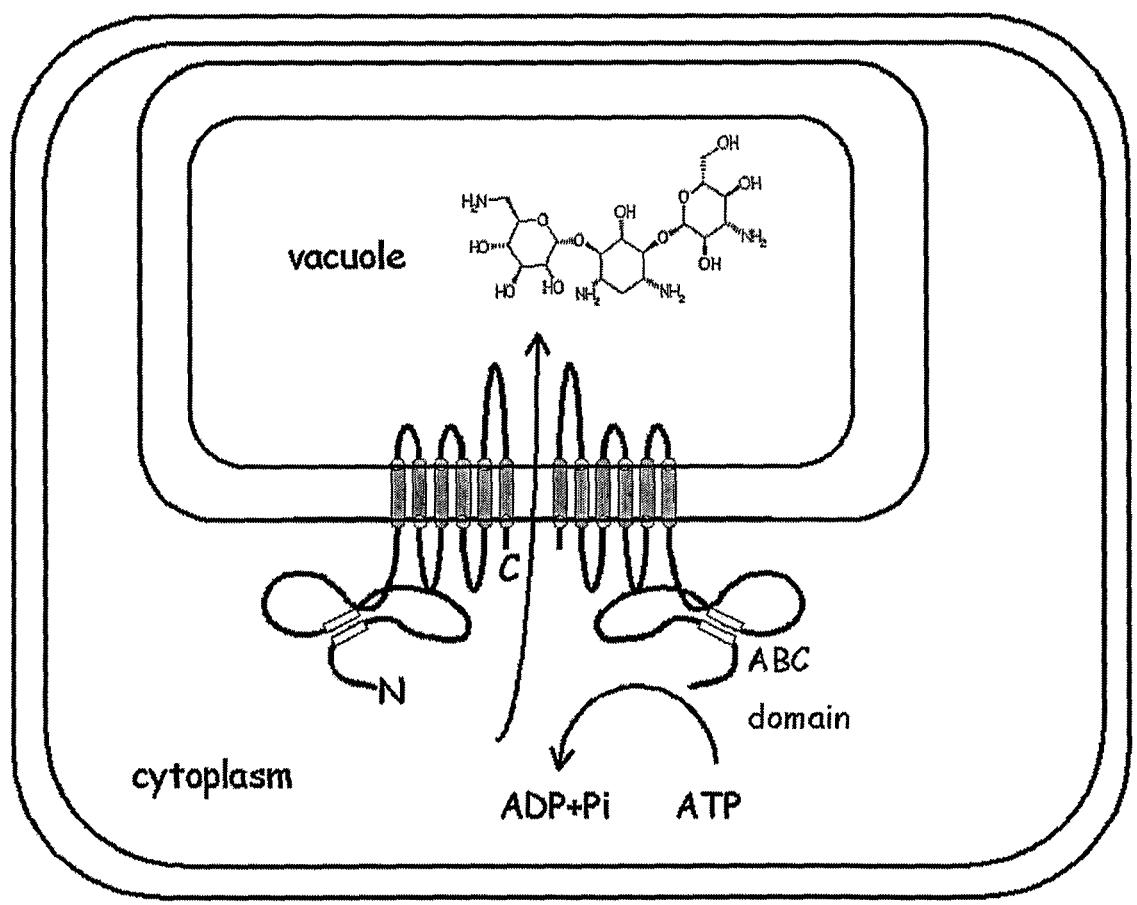
FIG. 4. Proposed mechanism of kanamycin resistance conferred by Atwbc19. AtWBC19 forms a homodimer that localizes to the vacuolar membrane. Kanamycin import to the vacuole is coupled with ATP hydrolysis. Sequestration of kanamycin into the vacuole prevents interference with ribosomal RNA in the cytoplasm, mitochondria and chloroplasts.

AtWBC19 apparently possesses a predicted domain organization typical of most members of WBC family consisting one ABC domain and one membrane-spanning domain consisting of six spans. Ten independent transgenic plants containing an Atwbc19-N-terminal gfp fusion construct were used in a preliminary examination of AtWBC19 cellular localization of. Epifluorescence microscopy revealed that GFP fluorescence in $T_0$ and $T_1$ plants could not be detected in aerial part of plants, but could be visualized in root tips (FIGS. 3A and 3B). GFP seemed to be directed to vacuoles and was definitely excluded from the nucleus (FIG. 3C). Because GFP is rapidly degraded in vacuoles under light, it is typically difficult to detect in aerial organs of higher plants (Tamura et al., 2003), thus the accumulation in roots in intact plants. Under confocal microscopy, GFP fluorescence was coincident with vacuoles isolated from transgenic protoplasts (FIGS. 3D, 3E, and 3F). Thus, the preliminary evidence indicates that AtWBC19 is targeted to the vacuole membrane, and we propose that kanamycin is actively sequestered in the vacuole as a substrate of this ABC transporter (FIG. 4). The sequestration of kanamycin into the vacuole would prevent its interference with ribosomal RNA in the cytoplasm, mitochondria and chloroplasts, thereby alleviating its toxicity.

Taken together these results demonstrate show that Atwbc19 is an effective selectable marker candidate as a substitute for nptII for the production of transgenic plants. To our knowledge, this is the first identified plant gene useful for conferring antibiotic resistance. The overwhelming majority of selectable markers currently in use in biotechnology are from bacterial origin (Miki et al., 2004). Although they are generally recognized as safe by many regulating agencies, concerns are constantly raised about unpredictable consequences to ecosystems or human health from horizontal gene transfer (HGT). Recent publications argue that HGT between transgenic plants and soil microorganisms might be underestimated and should be monitored (Heinemann et al., 2004; Nielsen et al., 2004) despite contradictory data and a priori biological hurdles for HGT (Davison, 2004). In this light, there are at least two strategies to address related biosafety issues of GM plants and improve public acceptance (Miki et al., 2004; Day et al., 2003). The first consists of producing marker-free plants whereby the selectable marker is removed by a variety of methods, including site-specific recombination, transposon mediated elimination, and co-transformation, followed by segregation. Such methods are either more difficult to implement or are less efficient than procedures that leave the marker genes in the plant (Miki et al., 2004; Day et al., 2003). The second, more comprehensive strategy is the use of plant genes, regulatory elements, T-DNA borders-like sequences and selectable markers originating from plants (Rommens et al., 2004a; Rommens et al., 2004b). Currently effective selectable markers derived from plants are lacking besides the herbicide resistance genes EPSP synthase and ALS. All other current plant selectable markers are suboptimal in practice or have negative consequences. For example, the TDC gene leads to tryptamine accumulation in transformed plants (Goddijn et al., 2003) whereas regeneration-promoting genes such as Atipt (Zuo et al., 2002) adversely affect plant growth and development when constitutively overexpressed. Therefore, they must be used with a tightly controlled inducible promoter or subsequently removed later.

We know of no such undesirable effects or limitations with use of Atwbc19 as a selection marker, since it amounts to harnessing plant's own genome for established kanamycin resistance procedures common for many species; a plug and play plant-based marker. Here we shown its usefulness as a selection market in tobacco, but it may prove to be particularly valuable for the transformation of agriculturally-important species extremely susceptible to kanamycin such as cotton and soybean (Liu et al., 2004; Zhang et al., 2001).

Plant Transformation, Segregation and Growth Analysis

Constructs were made in the binary vector pCAMBIA2301 (CAMBIA, Canberra, Australia). The CaMV 35S promoter and the nos terminator were introduced at the HindIII-XbaI and SacI-EcoRI sites to generate the empty vector pS15. Atwbc19 was PCR amplified from BAC clone T26I12 obtained from the *Arabidopsis* Biological Resource Center (Ohio State University, Columbus, USA). The forward (5'ACTGCAGGTACCATGAATCTATCACTCAGCGG 3') and reverse (5'TGTCCCCGTTTTTATCCAAG 3') primers used were designed to introduce KpnI and SacI sites. Atwbc19 was ligated into the appropriate location in pS15 resulting in pS15-ABC. Plasmid pS15-ABC-dKan was generated from pS15-ABC by removing the nptII gene by vector digestion with XhoI and religation (FIG. 1A).

*Agrobacterium tumefaciens* strain GV3850 was used for leaf disc transformation (Horsch et al., 1985) of *Nicotiana tabacum* cv Xanthi using either 50, 100 or 200 mg/l kanamycin disulfate (Sigma, St. Louis, Mo., USA) in addition to 200 mg/L timentin in the media (GlaxoSmithKline, Philadelphia, Pa., USA). For each selection regime and each plasmid a total of 48 to 56 explants were plated in 3 replicate experiments. The number of putative transgenic plants was recorded after transfer of rooted shoots to soil. GUS assays (Jefferson et al., 1987) were performed to assay transgene integration and expression.

Segregation analysis was performed on MS media (Murashige et al., 1962) with B5 vitamins (Gamborg et al., 1968) and 3% sucrose (MSO media) containing 200 mg/l kanamycin. $T_1$ seeds from plants transformed with pS15-ABC-dKan were surface sterilized and germinated on the media. Root growth analysis was performed as above on vertically positioned plates where 6 seeds per plate and 6 replicate plates for each event were germinated with and without 100 and 200 mg/l kanamycin. Root length was measured after 3 weeks. All experiments were performed in a 25° C. growth cabinet under constant 40 µE irradiance.

Southern Blot Analysis

Genomic DNA was extracted from leaf tissue of $T_0$ plants and 10 µg was digested with KpnI and SacI, to produce an expected 2.1 kb fragment in transgenic events corresponding with the coding region of Atwbc19. The digested DNA was separated on a 0.7% (w/v) agarose gel and blotted onto Hybond-Ny$^+$ (Amersham Phamiacia Biotech, Piscataway, N.J., USA). The Atwbc19 fragment was released from the plasmid pS15-ABC by KpnI and SacI digestion, eluted from the gel and radiolabelled with [$^{32}$P] using random primers and RadPrime DNA labeling system under manufacturer's instructions (Invitrogen, Carlsbad, Calif., USA). Autoradiographic exposures were captured using a Personal FX Phosphoimager (Bio-Rad, Hercules, Calif., USA).

Northern Blot Analysis

Selected transgenic events with single locus inserts (3:1 segregation; $X^2$ test, P<0.05) were selected for northern blot analysis. RNA was extracted using the Rneasy Mini Kit and manufacturer's protocol (Qiagen, Valencia, Calif., USA). Ten micrograms of RNA was loaded in each well. Plant RNA was transferred to a nylon membrane by capillary action and probed with Atwbc19 as above.

Subcellular Localization

Figure 7:
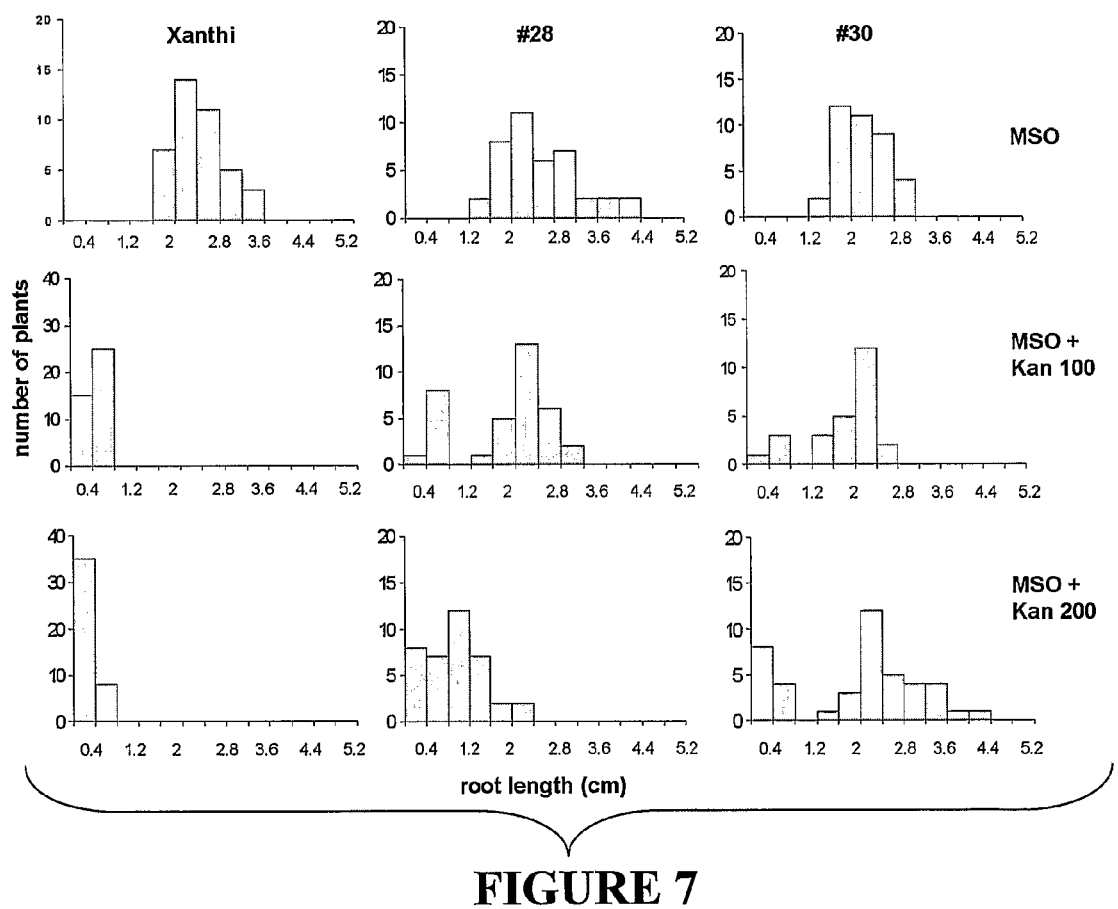
FIG. 7. Root length distribution frequency of nontransgenic tobacco (Xanthi), and $T_1$ transgenic lines 28 and 30 grown on MSO media with or without 100 or 200 mg/l kanamycin.

Construction of an N-terminal GFP fusion with Atwbc19 was performed by amplifying mgfp5-ER using forward primer 5'TGCAGGTACCATGAGTAAAGGAGAA-GAACTTTTC 3' and reverse primer 5'GCTAGGTAC-CTTTGTATAGTTCATCCATGCC 3'. The amplified fragment no longer had the signal sequence and the ER retention signal from mGFP5-ER. A start codon and KpnI sites were introduced on either ends that allowed in frame cloning into the KpnI site of pS15-ABC (FIG. 7). Roots and leaves from transgenic plants were examined under an epifluorescence microscope (Olympus BX51, Olympus, Melville, N.Y., USA) or a confocal laser scanning microscope (Leica TCS-SP2, Leica, Heidelberg GmbH, Germany). For confocal microscopy, GFP was excited at 488 nm using an argon laser, and fluorescence emission was recorded in the green channel (500 to 560 nm). To differentiate the GFP signal from chlorophyll autofluorescence in leaf mesophyll protoplasts, fluorescence was also recorded in the red channel (650-720 nm). In the merged image, a GFP specific signal appears green and background fluorescence appears as yellow.

EXAMPLE 3

Materials and Methods

Bacterial Strains and Plasmids

*Escherichia coli* DH5α was obtained from stock strains available within our lab. All strains were cultured on LB media. Three plasmids were used in this study. pKS-ABC contains the Atwbc19 gene under the control of the lacZ promoter in pBluescript II SK+; pKS-nptII contains the nptII gene with the lacZ promoter in pBluescript II SK+; and pKS is pBluescript II SK+ with no inserted genes as a control. The microorganisms were maintained in glycerol stocks and stored at −80° C. Working cultures were obtained by inoculating a loopful of culture into 50 ml LB broth supplemented with ampicillin (100 mg/l) and incubated at 37° C. for 24 hr.

Determining Susceptibility of *Escherichia coli* to Kanamycin

Inserts were sequenced at 5' and 3' ends. The gram-negative soil bacteria *Escherichia coli* were examined for resistance to varying levels of kanamycin prior to transformation experiments under own experimental conditions. Bacteria were grown overnight in 50 mL cultures to approximately $1 \times 10^9$ CFU/ml, serially diluted and plated on LB with kanamycin (0, 25, 50 and 100 mg/ml). Plates were incubated overnight at 37° C. and growth observed after 24 hr incubation. Only those strains that were susceptible (i.e. no growth) at the lowest level of kanamycin were used for the horizontal gene transfer experiments.

Transformation

*E. coli* DH5α were transformed with pKS, pKS-ABC, and pKS-nptII by freeze/thaw method (Hanahan 1983). The gram-negative soil bacteria *Escherichia coli* DH5α were used in all transformations. For selection of transformants, aliquots of bacteria were spread onto solidified LB medium supplemented with ampicillin (100 mg/l) and incubated at 37° C.

Assessment of New Antibiotic Resistance through Natural Transformation

Bacteria were observed for their ability to develop kanamycin resistance using 96-well microtiter plates. Isopropyl-b-D-thiogalctopyranoside (IPTG) at 1 mM was used to induce Atwbc19 expression. Each well was filled with 199 μl LB, IPTG and varying concentrations of kanamycin or gentamycin and 50 μl bacterial treatment (DH5α transformed with pKS-ABC, DH5α transformed with pKS-nptII, DH5α transformed with pKS or none). Each treatment was done in triplicate in sterile 96-well microtiter plates and each experiment was duplicated. Optical densities were measured at 630 nm (Biorad) after incubating microtiter plates at 37° C. for 24 hr.

Statistical Analysis

Data were analyzed by analysis of variance using the general linear model. Duncan's Multiple Range test was used to compare treatment mean values. Differences were considered significant at the 0.05 probability level. All analysis was performed using the SAS program (Statistic Analysis Systems 9.1, SAS Institute, Inc., Cary, N.C.).

Results

Figure 8:
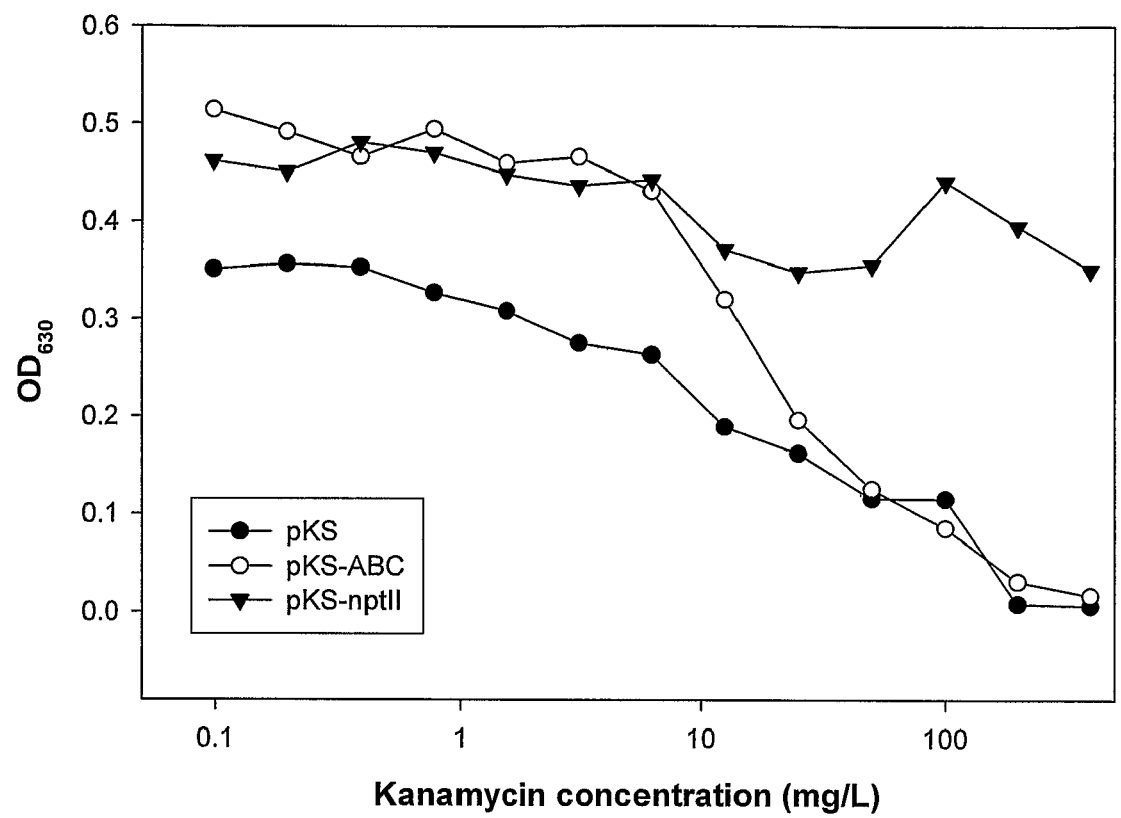
FIG. 8. Optical densities (630 nm) of *E. coli* DH5α transformed (pKS-ABC (n=12), pKS-nptII (n=12) or pKS (n=6)) when incubated in LB+IPTG with varying (A) kanamycin concentrations (0 to 400 mg/l).

Atwbc19 did confer resistance to lower concentrations of kanamycin to *E. coli* (below 12.5 mg/l). The nptII gene, however, provided greater resistance to kanamycin in *E. coli* than that of the Atwbc19 gene and was significantly different from the no-plasmid control at higher concentrations of kanamycin (e.g., over 10 mg/l) (p<0.05) (FIG. 8). The Atwbc19 gene was not significantly different from the no-plasmid control at higher concentrations of kanamycin (e.g., over 25 mg/l) (p<0.05). *E. coli* transformed with pKS-ABC showed little resistance to kanamycin at 100 mg/l (FIG. 8). NptII, however, demonstrated kanamycin resistance at the 100 mg/l concentration as well at the 400 mg/l, the highest concentration tested (FIG. 8).

REFERENCES

Bevan, M. W., Flavell, R. B., & Chilton, M. D. (1983) "A chimaeric antibiotic-resistance gene as a selectable marker for plant-cell transformation" *Nature* 304:184-187.

Davison, J. (2004) "Monitoring horizontal gene transfer" *Nat. Biotechnol.* 22:1349.

Day, A. (2003) "Antibiotic resistance genes in transgenic plants: their origins, undesirability and technologies fir their elimination" In: *Transgenic Plants: Current Innovations and Future Trends*. Stewart C. N., Jr. (Ed.), pp. 111-156, Horizon Scientific Press, Wymondham, England.

Fraley, R. T., Rogers, S. G., Horsch, R. B., Sanders, P. R., Flick, J. S., Adams, S. P., Bittner, M. L., Brand, L. A., Fink, C. L., Fry, J. S., Galluppi, G. R., Goldberg, S. B., Hoffmann, N. L., & Woo, S. C. (1983) "Expression of bacterial genes in plant cells" *Proc. Natl. Acad. Sci. U.S.A.* 80:4803-4807.

Gamborg, O. L., Miller, R. A., & Ojima, K. (1968) "Nutrient requirements of suspension cultures of soybean root cells" *Exp. Cell Res.* 50:158.

Goddijn, O. J., van der Duyn Schouten, P. M., Schilperoort, R. A., & Hoge, J. H. (1993) "A chimaeric tryptophan decarboxylase gene as a novel selectable marker in plant cells" *Plant Mol. Biol.* 22:907-912.

Heinemann, J. A. & Traavik, T. (2004) "Problems in monitoring horizontal gene transfer in field trials of transgenic plants" *Nat. Biotechnol.* 22:1105-1109.

Herrera-Estrella, L., Deblock, M., Messens, E., Hernalsteens, J. P., Vanmontagu, M., & Schell, J. (1983) "Chimeric genes as dominant selectable markers in plant cells" *EMBO J.* 2:987-995.

Higgins, C. F. (1992) "ABC transporters—from microorganisms to man" *Annu. Rev. Cell Biol.* 8:67-113.

Horsch, R. B., Fry, J. E., Hoffmann, N. L., Eichholtz, D., Rogers, S. G., & Fraley, R. T. (1985) "A simple and general-method for transferring genes into plants" *Science* 227:1229-1231.

Jefferson, R. A., Kavanagh, T. A., & Bevan, M. W. (1987) "GUS fusions: beta-glucuronidase as a sensitive and versatile gene fusion marker in higher plants" *EMBO J.* 6:3901-3907.

Liu, H. K., Yang, C., & Wei, Z. M. (2004) "Efficient *Agrobacterium tumefaciens*-mediated transformation of soybeans using an embryonic tip regeneration system" *Planta* 219:1042-1049.

Mentewab, A., Cardoza, V., & Stewart, J. (2005) "Genomic analysis of the response of *Arabidopsis thaliana* to trinitrotoluene as revealed by cDNA microarrays" *Plant Sci.* In Press.

Mingeot-Leclercq, M. P., Glupczynski, Y., & Tulkens, P. M. (1999) "Aminoglycosides: activity and resistance" *Antimicrob. Agents Chemother.* 43:727-737.

Miki, B. & McHugh, S. (2004) "Selectable marker genes in transgenic plants: applications, alternatives and biosafety" *J. Biotechnol.* 107:193-232.

Murashige T. & Skoog F. (1962) "A revised medium for rapid growth and bioassays with tobacco tissue culture" *Physiol. Plant.* 15:497.

Nielsen, K. M. & Townsend, J. P. (2004) "Monitoring and modeling horizontal gene transfer" *Nat. Biotechnol.* 22, 1110-1114.

Pighin, J. A., Zheng, H. Q., Balakshin, L. J., Goodman, I. P., Western, T. L., Jetter, R., Kunst, L.; & Samuels, A. L. (2004) "Plant cuticular lipid export requires an ABC transporter" *Science* 306:702-704.

Rommens, C. M., Humara, J. M., Ye, J. S., Yan, H., Richael, C., Zhang, L., Perry, R., & Swords, K. (2004a) "Crop improvement through modification of the plant's own genome. *Plant Physiol.* 135:421-431.

Rommens, C. M. (2004b) "All-native DNA transformation: a new approach to plant genetic engineering" *Trends Plant Sci.* 9:457-464.

Sanchez-Fernandez, R., Rea, P. A., Davies, T. G., & Coleman, J. O. (2001a) "Do plants have more genes than humans? Yes, when it comes to ABC proteins" *Trends Plant Sci.* 6:347-348.

Sanchez-Fernandez, R., Davies, T. G. E., Coleman, J. O. D., & Rea, P. A. The *Arabidopsis thaliana* (2001b) "ABC protein superfamily, a complete inventory" *J. Biol. Chem.* 276:30231-30244.

Shaked, Hezi, Melamed-Bessudo, Cathy, Levy, Avraham A. (2005) "High-frequency gene targeting in *Arabidopsis* plants expressing the yeast RAD54 gene" *PNAS* 102(34): 12265-12269.

Tamura, K., Shimada, T., Ono, E., Tanaka, Y., Nagatani, A., Higashi, S., Watanabe, M., Nishimura, M., & Hara-Nishimura, I. (2003) "Why green fluorescent fusion proteins have not been observed in the vacuoles of higher plants" *Plant J.* 35:545-555.

Wright, G. D., Berghuis, A. M., & Mobashery, S. (1998) "Aminoglycoside antibiotics—structures, functions, and resistance" *Adv. Exp. Med. Biol.* 456:27-69.

Zhang, B. H., Liu, F., Liu, Z. H., Wang, H. M., & Yao, C. B. (2001) "Effects of kanamycin on tissue culture and somatic embryogenesis in cotton" *Plant Growth Regul.* 33:137-149.

Zuo, J. R., Niu, Q. W., Ikeda, Y., & Chua, N. H. (2002) "Marker-free transformation: increasing transformation frequency by the use of regeneration—promoting genes" *Curr. Opin. Biotech.* 13:173-180.

We claim:

1. A method of imparting kanamycin resistance to a plant, plant cell, or plant part susceptible to kanamycin comprising:
   a) obtaining a plant, plant cell, or plant part that is susceptible or sensitive to kanamycin; and
   b) transforming said plant, plant cell, or plant part with a polynucleotide encoding an polypeptide comprising SEQ ID NO: 2.

2. The method according to claim 1, wherein said polynucleotide comprises SEQ ID NO: 1 or SEQ ID NO: 3.

3. The method according to claim 2, wherein said polynucleotide comprises SEQ ID NO: 1.

4. The method according to claim 2, wherein said polynucleotide comprises SEQ ID NO: 3.

5. The method according to claim 2, further comprising growing said transformed cell in the presence of kanamycin and identifying plants, plant cells, or plant parts that are resistant to kanamycin.

6. The method according to claim 1, further comprising growing said transformed cell in the presence of kanamycin and identifying plants, plant cells, or plant parts that are resistant to kanamycin.

7. The method according to claim 1, wherein said plant, plant cell, or plant part further comprises a heterologous gene of interest.

8. The method according to claim 1, further comprising transforming said plant, plant cell, or plant part with a heterologous gene of interest.

9. A method of imparting kanamycin resistance to a plant, plant cell, or plant part susceptible to kanamycin comprising:
   a) obtaining a plant, plant cell, or plant part that is susceptible or sensitive to kanamycin; and
   b) transforming said plant, plant cell, or plant part with a heterologous promoter that is operably linked to a polynucleotide encoding a polypeptide comprising SEQ ID NO: 2.

10. The method according to claim 9, wherein said polynucleotide comprises SEQ ID NO: 1 or SEQ ID NO: 3.

11. The method according to claim 10, further comprising growing said transformed cell in the presence of kanamycin and identifying plants, plant cells, or plant parts that are resistant to kanamycin.

12. The method according to claim 9, further comprising growing said transformed cell in the presence of kanamycin and identifying plants, plant cells, or plant parts that are resistant to kanamycin.

* * * * *

UNITED STATES PATENT AND TRADEMARK OFFICE
CERTIFICATE OF CORRECTION

| | | |
|---|---|---|
| PATENT NO. | : 7,973,213 B2 | Page 1 of 1 |
| APPLICATION NO. | : 11/912713 | |
| DATED | : July 5, 2011 | |
| INVENTOR(S) | : C. Neal Stewart, Jr. and Mentewab Ayalew | |

It is certified that error appears in the above-identified patent and that said Letters Patent is hereby corrected as shown below:

Column 2,
Line 64, "Bar-20" should read --Bar=20--.

Column 4,
Line 61, "fall length" should read --full length--.

Signed and Sealed this
Twenty-seventh Day of September, 2011

David J. Kappos
*Director of the United States Patent and Trademark Office*

SEQUENCE LISTING

```
<160> NUMBER OF SEQ ID NOS: 6

<210> SEQ ID NO 1
<211> LENGTH: 2513
<212> TYPE: DNA
<213> ORGANISM: Arabidposis thaliana
<220> FEATURE:
<221> NAME/KEY: misc_feature
<222> LOCATION: (1)..(2513)
<223> OTHER INFORMATION: NCBI Nucleotide Accession No. NM_115371

<400> SEQUENCE: 1
atcataaaaa atatcactac taagaacttt cagattccac catatatact tcacaatcag      60
tttgatgatt tcttaagcca aaactctaaa cgacgccgtc cgatgaatct atcactcagc     120
ggtagaaaga ttgccatgac acgtgtttcg gcggaaactc agtatatcac tcccatcgga     180
tcaccaaccc tcgacgagtt gctgaaagac tgcgacagtt tccgaaaagg agattccggc     240
gacggcgtaa aaagcgacga tcctgcacat cacataatag atgtcgaagc cttgtacgta     300
aaacctgtcc cgtacgtctt aaactttaac aatcttcaat acgatgtcac acttcgccgg     360
cggtttggct tctcacggca aaacggagta aagactctac tcgatgatgt ttccggagag     420
gcttctgacg gcgatatcct cgccgttctc ggtgcaagtg gagcaggaaa atcaacgttg     480
atcgatgcac tagcggggag agttgctgag ggaagcttga gaggctctgt aactctaaac     540
ggagagaaag ttttgcaatc tcgattgttg aaagttatat cggcgtatgt tatgcaagac     600
gatcttcttt ttccgatgct caccgttaaa gaaaccctaa tgttcgcttc cgagtttcgt     660
```

```
ctcccgagaa gtttgtctaa gtcgaagaag atggagcgtg ttgaagccct aattgatcaa      720
ttagggttaa gaaacgcggc gaacacggta atcggagacg aaggacaccg tggagtttct      780
ggaggagaga gacggcgcgt ttcaatcgga atcgatatta tacacgatcc tatcgtcttg      840
ttcctcgacg aaccaacgtc ggggctggat tctacaaacg cgtttatggt ggtgcaagtt      900
ttgaaacgaa ttgctcaaag tggcagtatc gtaattatgt cgatccatca acctagtgct      960
cgaatcgtgg agttgcttga tcggcttatc attctatctc gtggcaaaag tgtgttcaat     1020
ggatctccgg cgagtcttcc cggattcttc tccgacttcg tcgtccgat cccggagaaa      1080 gagaacatat cagagttcgc acttgattta gttcgagagc ttgaaggatc caatgaaggt     1140
acgaaagctt tagtagactt caacgaaaag tggcaacaaa acaagatcag cctgatccaa     1200
tctgctccac aaaccaataa gctcgaccaa gaccgttcat tatctttaaa agaagccatt     1260
aatgcgagtg tttctagagg caaactagtc tcaggctcat ctagatccaa tcccacttcc     1320
atggaaacag tatcttcata cgcaaacccg tcgttgttcg aaacattcat cttagccaaa     1380
cggtacatga aaaactggat ccggatgcct gagctagtag aacaaggat tgctacggta      1440 atggtgactg gttgtctttt agcaactgtg tattggaagc tagaccacac tccaagagga     1500
gcacaagaga gattgacttt gttcgcattt gtcgtcccaa caatgttcta ttgttgttta     1560
gacaatgtcc ccgtttttat ccaagaacga tacatttttct taagagagac aacacacaac     1620
gcgtacagaa catcttcata cgtcatatca cactctcttg tgtccctgcc tcagctactt     1680
gcaccttcct tggtattttc cgcgatcaca ttctggaccg ttggattgag cggggggatta     1740 gagggttttg tcttctattg cctcctaatc tatgcctcct tttggtctgg atcttccgtc     1800 gttacctta tatccggtgt tgttccgaat atcatgttat gttacatggt ctccattacc      1860
tatctcgcct actgtttact gttgagtgga ttctacgtca accgagatcg aataccgttt     1920
tattggacgt ggtttcatta catttcaatt ctcaagtatc cgtatgaggc tgtcttaatc     1980
aacgagtttg atgacccgtc tcgttgtttt gttaggggtg tccaggtttt cgacagtact     2040
cttctcgggg gagtgtctga ctccgggaag gttaagctcc ttgaaactct cagtaaatct     2100
ctgagaacga agataacgga gtccacatgc ttgaggacgg ggtctgactt acttgcacaa     2160
cagggtatta cgcaattgag caagtgggat tgcttgtgga ttacgtttgc ttcaggtctc     2220
ttctttagga tcttatttta cttcgccttg ctgtttggga gcaggaataa gaggacgtga     2280
ggttactact tactagcgcc cacaaataca tttgtgcgca ttagctacat atttaagtga     2340
agcttgaaga attagcttct cgatgttact atacatttgt gaagaagttg taaaatttat     2400
actcatttca tctttgtttc tttaaaagaa tatactgtaa aataaacaag tatttcttct     2460
taaatatcca aattagcatc tgattacttg aatacacatt taaatttcga ggc           2513
```

<210> SEQ ID NO 2
<211> LENGTH: 725
<212> TYPE: PRT
<213> ORGANISM: Arabidopsis thaliana
<220> FEATURE:
<221> NAME/KEY: MISC_FEATURE
<222> LOCATION: (1)..(725)
<223> OTHER INFORMATION: ABC transporter family protein - NCBI
      Nucleotide Accession No. NM_115371
<220> FEATURE:
<221> NAME/KEY: MISC_FEATURE
<222> LOCATION: (1)..(725)
<223> OTHER INFORMATION: NCBI Protein Accession No. CAB75747
<220> FEATURE:
<221> NAME/KEY: MISC_FEATURE
<222> LOCATION: (1)..(725)

```
<223> OTHER INFORMATION: CDS 103..2280
<220> FEATURE:
<221> NAME/KEY: MISC_FEATURE
<222> LOCATION: (1)..(725)
<223> OTHER INFORMATION: locus_tag="At3g55130
<220> FEATURE:
<221> NAME/KEY: MISC_FEATURE
<222> LOCATION: (1)..(725)
<223> OTHER INFORMATION: note="breast cancer resistance protein 1 BCRP1,
      Mus musculus, EMBL:NP_036050; go_function:  ATP-binding cassette
      (ABC) transporter activity [goid 0004009]"
<220> FEATURE:
<221> NAME/KEY: MISC_FEATURE
<222> LOCATION: (1)..(725)
<223> OTHER INFORMATION: codon_start = 1
      product="ABC transporter family protein"
      protein id="NP_191073.1"
<220> FEATURE:
<221> NAME/KEY: MISC_FEATURE
<222> LOCATION: (1)..(725)
<223> OTHER INFORMATION: db_xref="GI:15233191"
<220> FEATURE:
<221> NAME/KEY: MISC_FEATURE
<222> LOCATION: (1)..(725)
<223> OTHER INFORMATION: db_xref="GeneID:824679"

<400> SEQUENCE: 2

Met Asn Leu Ser Leu Ser Gly Arg Lys Ile Ala Met Thr Arg Val Ser
1               5                   10                  15

Ala Glu Thr Gln Tyr Ile Thr Pro Ile Gly Ser Pro Thr Leu Asp Glu
            20                  25                  30

Leu Leu Lys Asp Cys Asp Ser Phe Arg Lys Gly Asp Ser Gly Asp Gly
        35                  40                  45

Val Lys Ser Asp Asp Pro Ala His His Ile Ile Asp Val Glu Ala Leu
    50                  55                  60

Tyr Val Lys Pro Val Pro Tyr Val Leu Asn Phe Asn Asn Leu Gln Tyr
65                  70                  75                  80

Asp Val Thr Leu Arg Arg Arg Phe Gly Phe Ser Arg Gln Asn Gly Val
                85                  90                  95

Lys Thr Leu Leu Asp Asp Val Ser Gly Glu Ala Ser Asp Gly Asp Ile
            100                 105                 110

Leu Ala Val Leu Gly Ala Ser Gly Ala Gly Lys Ser Thr Leu Ile Asp
        115                 120                 125

Ala Leu Ala Gly Arg Val Ala Glu Gly Ser Leu Arg Gly Ser Val Thr
    130                 135                 140

Leu Asn Gly Glu Lys Val Leu Gln Ser Arg Leu Leu Lys Val Ile Ser
145                 150                 155                 160

Ala Tyr Val Met Gln Asp Asp Leu Leu Phe Pro Met Leu Thr Val Lys
                165                 170                 175

Glu Thr Leu Met Phe Ala Ser Glu Phe Arg Leu Pro Arg Ser Leu Ser
            180                 185                 190

Lys Ser Lys Lys Met Glu Arg Val Glu Ala Leu Ile Asp Gln Leu Gly
        195                 200                 205

Leu Arg Asn Ala Ala Asn Thr Val Ile Gly Asp Glu Gly His Arg Gly
    210                 215                 220

Val Ser Gly Gly Glu Arg Arg Arg Val Ser Ile Gly Ile Asp Ile Ile
225                 230                 235                 240

His Asp Pro Ile Val Leu Phe Leu Asp Glu Pro Thr Ser Gly Leu Asp
                245                 250                 255

Ser Thr Asn Ala Phe Met Val Val Gln Val Leu Lys Arg Ile Ala Gln
            260                 265                 270

Ser Gly Ser Ile Val Ile Met Ser Ile His Gln Pro Ser Ala Arg Ile
```

```
                275                 280                 285
Val Glu Leu Leu Asp Arg Leu Ile Ile Leu Ser Arg Gly Lys Ser Val
290                 295                 300
Phe Asn Gly Ser Pro Ala Ser Leu Pro Gly Phe Phe Ser Asp Phe Gly
305                 310                 315                 320
Arg Pro Ile Pro Glu Lys Glu Asn Ile Ser Glu Phe Ala Leu Asp Leu
                325                 330                 335
Val Arg Glu Leu Glu Gly Ser Asn Glu Gly Thr Lys Ala Leu Val Asp
            340                 345                 350
Phe Asn Glu Lys Trp Gln Gln Asn Lys Ile Ser Leu Ile Gln Ser Ala
        355                 360                 365
Pro Gln Thr Asn Lys Leu Asp Gln Asp Arg Ser Leu Ser Leu Lys Glu
    370                 375                 380
Ala Ile Asn Ala Ser Val Ser Arg Gly Lys Leu Val Ser Gly Ser Ser
385                 390                 395                 400
Arg Ser Asn Pro Thr Ser Met Glu Thr Val Ser Ser Tyr Ala Asn Pro
                405                 410                 415
Ser Leu Phe Glu Thr Phe Ile Leu Ala Lys Arg Tyr Met Lys Asn Trp
            420                 425                 430
Ile Arg Met Pro Glu Leu Val Gly Thr Arg Ile Ala Thr Val Met Val
        435                 440                 445
Thr Gly Cys Leu Leu Ala Thr Val Tyr Trp Lys Leu Asp His Thr Pro
    450                 455                 460
Arg Gly Ala Gln Glu Arg Leu Thr Leu Phe Ala Phe Val Val Pro Thr
465                 470                 475                 480
Met Phe Tyr Cys Cys Leu Asp Asn Val Pro Val Phe Ile Gln Glu Arg
                485                 490                 495
Tyr Ile Phe Leu Arg Glu Thr Thr His Asn Ala Tyr Arg Thr Ser Ser
            500                 505                 510
Tyr Val Ile Ser His Ser Leu Val Ser Leu Pro Gln Leu Leu Ala Pro
        515                 520                 525
Ser Leu Val Phe Ser Ala Ile Thr Phe Trp Thr Val Gly Leu Ser Gly
    530                 535                 540
Gly Leu Glu Gly Phe Val Phe Tyr Cys Leu Leu Ile Tyr Ala Ser Phe
545                 550                 555                 560
Trp Ser Gly Ser Ser Val Thr Phe Ile Ser Gly Val Val Pro Asn
                565                 570                 575
Ile Met Leu Cys Tyr Met Val Ser Ile Thr Tyr Leu Ala Tyr Cys Leu
            580                 585                 590
Leu Leu Ser Gly Phe Tyr Val Asn Arg Asp Arg Ile Pro Phe Tyr Trp
        595                 600                 605
Thr Trp Phe His Tyr Ile Ser Ile Leu Lys Tyr Pro Tyr Glu Ala Val
    610                 615                 620
Leu Ile Asn Glu Phe Asp Asp Pro Ser Arg Cys Phe Val Arg Gly Val
625                 630                 635                 640
Gln Val Phe Asp Ser Thr Leu Leu Gly Gly Val Ser Asp Ser Gly Lys
                645                 650                 655
Val Lys Leu Leu Glu Thr Leu Ser Lys Ser Leu Arg Thr Lys Ile Thr
            660                 665                 670
Glu Ser Thr Cys Leu Arg Thr Gly Ser Asp Leu Leu Ala Gln Gln Gly
        675                 680                 685
Ile Thr Gln Leu Ser Lys Trp Asp Cys Leu Trp Ile Thr Phe Ala Ser
    690                 695                 700
```

```
Gly Leu Phe Phe Arg Ile Leu Phe Tyr Phe Ala Leu Leu Phe Gly Ser
705                 710                 715                 720

Arg Asn Lys Arg Thr
                725

<210> SEQ ID NO 3
<211> LENGTH: 2513
<212> TYPE: DNA
<213> ORGANISM: Arabidopsis thaliana
<220> FEATURE:
<221> NAME/KEY: misc_feature
<222> LOCATION: (1)..(2513)
<223> OTHER INFORMATION: NCBI Nucleotide Accession No. NM_115371
<220> FEATURE:
<221> NAME/KEY: CDS
<222> LOCATION: (103)..(2280)

<400> SEQUENCE: 3
atcataaaaa atatcactac taagaacttt cagattccac catatatact tcacaatcag      60
tttgatgatt tcttaagcca aaactctaaa cgacgccgtc cg atg aat cta tca       114
                                            Met Asn Leu Ser
                                              1 ctc agc ggt aga aag att gcc atg aca cgt gtt tcg gcg gaa act cag     162
Leu Ser Gly Arg Lys Ile Ala Met Thr Arg Val Ser Ala Glu Thr Gln
  5              10                  15                  20 tat atc act ccc atc gga tca cca acc ctc gac gag ttg ctg aaa gac     210
Tyr Ile Thr Pro Ile Gly Ser Pro Thr Leu Asp Glu Leu Leu Lys Asp
             25                  30                  35 tgc gac agt ttc cga aaa gga gat tcc ggc gac ggc gta aaa agc gac     258
Cys Asp Ser Phe Arg Lys Gly Asp Ser Gly Asp Gly Val Lys Ser Asp
         40                  45                  50 gat cct gca cat cac ata ata gat gtc gaa gcc ttg tac gta aaa cct     306
Asp Pro Ala His His Ile Ile Asp Val Glu Ala Leu Tyr Val Lys Pro
     55                  60                  65 gtc ccg tac gtc tta aac ttt aac aat ctt caa tac gat gtc aca ctt     354
Val Pro Tyr Val Leu Asn Phe Asn Asn Leu Gln Tyr Asp Val Thr Leu
 70                  75                  80 cgc cgg cgg ttt ggc ttc tca cgg caa aac gga gta aag act cta ctc     402
Arg Arg Arg Phe Gly Phe Ser Arg Gln Asn Gly Val Lys Thr Leu Leu
85                  90                  95                 100 gat gat gtt tcc gga gag gct tct gac ggc gat atc ctc gcc gtt ctc     450
Asp Asp Val Ser Gly Glu Ala Ser Asp Gly Asp Ile Leu Ala Val Leu
                105                 110                 115 ggt gca agt gga gca gga aaa tca acg ttg atc gat gca cta gcg ggg     498
Gly Ala Ser Gly Ala Gly Lys Ser Thr Leu Ile Asp Ala Leu Ala Gly
            120                 125                 130 aga gtt gct gag gga agc ttg aga ggc tct gta act cta aac gga gag     546
Arg Val Ala Glu Gly Ser Leu Arg Gly Ser Val Thr Leu Asn Gly Glu
        135                 140                 145 aaa gtt ttg caa tct cga ttg ttg aaa gtt ata tcg gcg tat gtt atg     594
Lys Val Leu Gln Ser Arg Leu Leu Lys Val Ile Ser Ala Tyr Val Met
    150                 155                 160 caa gac gat ctt ctt ttt ccg atg ctc acc gtt aaa gaa acc cta atg     642
Gln Asp Asp Leu Leu Phe Pro Met Leu Thr Val Lys Glu Thr Leu Met
165                 170                 175                 180 ttc gct tcc gag ttt cgt ctc ccg aga agt ttg tct aag tcg aag aag     690
Phe Ala Ser Glu Phe Arg Leu Pro Arg Ser Leu Ser Lys Ser Lys Lys
                185                 190                 195 atg gag cgt gtt gaa gcc cta att gat caa tta ggg tta aga aac gcg     738
Met Glu Arg Val Glu Ala Leu Ile Asp Gln Leu Gly Leu Arg Asn Ala
            200                 205                 210 gcg aac acg gta atc gga gac gaa gga cac cgt gga gtt tct gga gga     786
```

|  |  |  |  |  |  |  |  |  |  |  |  |  |  |
|---|---|---|---|---|---|---|---|---|---|---|---|---|---|
| Ala | Asn | Thr | Val | Ile | Gly | Asp | Glu | Gly | His | Arg | Gly | Val | Ser | Gly | Gly |
|  |  |  | 215 |  |  |  | 220 |  |  |  | 225 |  |  |

| gag | aga | cgg | cgc | gtt | tca | atc | gga | atc | gat | att | ata | cac | gat | cct | atc | 834 |
|---|---|---|---|---|---|---|---|---|---|---|---|---|---|---|---|---|
| Glu | Arg | Arg | Arg | Val | Ser | Ile | Gly | Ile | Asp | Ile | Ile | His | Asp | Pro | Ile |  |
| 230 |  |  |  |  | 235 |  |  |  |  | 240 |  |  |  |  |  |  |

| gtc | ttg | ttc | ctc | gac | gaa | cca | acg | tcg | ggg | ctg | gat | tct | aca | aac | gcg | 882 |
| Val | Leu | Phe | Leu | Asp | Glu | Pro | Thr | Ser | Gly | Leu | Asp | Ser | Thr | Asn | Ala |  |
| 245 |  |  |  |  | 250 |  |  |  |  | 255 |  |  |  |  | 260 |  |

| ttt | atg | gtg | gtg | caa | gtt | ttg | aaa | cga | att | gct | caa | agt | ggc | agt | atc | 930 |
| Phe | Met | Val | Val | Gln | Val | Leu | Lys | Arg | Ile | Ala | Gln | Ser | Gly | Ser | Ile |  |
|  |  |  |  | 265 |  |  |  |  | 270 |  |  |  |  | 275 |  |  |

| gta | att | atg | tcg | atc | cat | caa | cct | agt | gct | cga | atc | gtg | gag | ttg | ctt | 978 |
| Val | Ile | Met | Ser | Ile | His | Gln | Pro | Ser | Ala | Arg | Ile | Val | Glu | Leu | Leu |  |
|  |  |  | 280 |  |  |  |  | 285 |  |  |  |  | 290 |  |  |  |

| gat | cgg | ctt | atc | att | cta | tct | cgt | ggc | aaa | agt | gtg | ttc | aat | gga | tct | 1026 |
| Asp | Arg | Leu | Ile | Ile | Leu | Ser | Arg | Gly | Lys | Ser | Val | Phe | Asn | Gly | Ser |  |
|  |  | 295 |  |  |  |  | 300 |  |  |  |  | 305 |  |  |  |  |

| ccg | gcg | agt | ctt | ccc | gga | ttc | ttc | tcc | gac | ttc | ggt | cgt | ccg | atc | ccg | 1074 |
| Pro | Ala | Ser | Leu | Pro | Gly | Phe | Phe | Ser | Asp | Phe | Gly | Arg | Pro | Ile | Pro |  |
|  | 310 |  |  |  |  | 315 |  |  |  |  | 320 |  |  |  |  |  |

| gag | aaa | gag | aac | ata | tca | gag | ttc | gca | ctt | gat | tta | gtt | cga | gag | ctt | 1122 |
| Glu | Lys | Glu | Asn | Ile | Ser | Glu | Phe | Ala | Leu | Asp | Leu | Val | Arg | Glu | Leu |  |
| 325 |  |  |  |  | 330 |  |  |  |  | 335 |  |  |  |  | 340 |  |

| gaa | gga | tcc | aat | gaa | ggt | acg | aaa | gct | tta | gta | gac | ttc | aac | gaa | aag | 1170 |
| Glu | Gly | Ser | Asn | Glu | Gly | Thr | Lys | Ala | Leu | Val | Asp | Phe | Asn | Glu | Lys |  |
|  |  |  |  | 345 |  |  |  |  | 350 |  |  |  |  | 355 |  |  |

| tgg | caa | caa | aac | aag | atc | agc | ctg | atc | caa | tct | gct | cca | caa | acc | aat | 1218 |
| Trp | Gln | Gln | Asn | Lys | Ile | Ser | Leu | Ile | Gln | Ser | Ala | Pro | Gln | Thr | Asn |  |
|  |  |  | 360 |  |  |  |  | 365 |  |  |  |  | 370 |  |  |  |

| aag | ctc | gac | caa | gac | cgt | tca | tta | tct | tta | aaa | gaa | gcc | att | aat | gcg | 1266 |
| Lys | Leu | Asp | Gln | Asp | Arg | Ser | Leu | Ser | Leu | Lys | Glu | Ala | Ile | Asn | Ala |  |
|  |  | 375 |  |  |  |  | 380 |  |  |  |  | 385 |  |  |  |  |

| agt | gtt | tct | aga | ggc | aaa | cta | gtc | tca | ggc | tca | tct | aga | tcc | aat | ccc | 1314 |
| Ser | Val | Ser | Arg | Gly | Lys | Leu | Val | Ser | Gly | Ser | Ser | Arg | Ser | Asn | Pro |  |
|  | 390 |  |  |  |  | 395 |  |  |  |  | 400 |  |  |  |  |  |

| act | tcc | atg | gaa | aca | gta | tct | tca | tac | gca | aac | ccg | tcg | ttg | ttc | gaa | 1362 |
| Thr | Ser | Met | Glu | Thr | Val | Ser | Ser | Tyr | Ala | Asn | Pro | Ser | Leu | Phe | Glu |  |
| 405 |  |  |  |  | 410 |  |  |  |  | 415 |  |  |  |  | 420 |  |

| aca | ttc | atc | tta | gcc | aaa | cgg | tac | atg | aaa | aac | tgg | atc | cgg | atg | cct | 1410 |
| Thr | Phe | Ile | Leu | Ala | Lys | Arg | Tyr | Met | Lys | Asn | Trp | Ile | Arg | Met | Pro |  |
|  |  |  |  | 425 |  |  |  |  | 430 |  |  |  |  | 435 |  |  |

| gag | cta | gta | gga | aca | agg | att | gct | acg | gta | atg | gtg | act | ggt | tgt | ctt | 1458 |
| Glu | Leu | Val | Gly | Thr | Arg | Ile | Ala | Thr | Val | Met | Val | Thr | Gly | Cys | Leu |  |
|  |  |  | 440 |  |  |  |  | 445 |  |  |  |  | 450 |  |  |  |

| tta | gca | act | gtg | tat | tgg | aag | cta | gac | cac | act | cca | aga | gga | gca | caa | 1506 |
| Leu | Ala | Thr | Val | Tyr | Trp | Lys | Leu | Asp | His | Thr | Pro | Arg | Gly | Ala | Gln |  |
|  |  | 455 |  |  |  |  | 460 |  |  |  |  | 465 |  |  |  |  |

| gag | aga | ttg | act | ttg | ttc | gca | ttt | gtc | gtc | cca | aca | atg | ttc | tat | tgt | 1554 |
| Glu | Arg | Leu | Thr | Leu | Phe | Ala | Phe | Val | Val | Pro | Thr | Met | Phe | Tyr | Cys |  |
| 470 |  |  |  |  | 475 |  |  |  |  | 480 |  |  |  |  |  |  |

| tgt | tta | gac | aat | gtc | ccc | gtt | ttt | atc | caa | gaa | cga | tac | att | ttc | tta | 1602 |
| Cys | Leu | Asp | Asn | Val | Pro | Val | Phe | Ile | Gln | Glu | Arg | Tyr | Ile | Phe | Leu |  |
| 485 |  |  |  |  | 490 |  |  |  |  | 495 |  |  |  |  | 500 |  |

| aga | gag | aca | aca | cac | aac | gcg | tac | aga | aca | tct | tca | tac | gtc | ata | tca | 1650 |
| Arg | Glu | Thr | Thr | His | Asn | Ala | Tyr | Arg | Thr | Ser | Ser | Tyr | Val | Ile | Ser |  |
|  |  |  |  | 505 |  |  |  |  | 510 |  |  |  |  | 515 |  |  |

| cac | tct | ctt | gtg | tcc | ctg | cct | cag | cta | ctt | gca | cct | tcc | ttg | gta | ttt | 1698 |
| His | Ser | Leu | Val | Ser | Leu | Pro | Gln | Leu | Leu | Ala | Pro | Ser | Leu | Val | Phe |  |
|  |  | 520 |  |  |  |  | 525 |  |  |  |  | 530 |  |  |  |  |

| tcc | gcg | atc | aca | ttc | tgg | acc | gtt | gga | ttg | agc | ggg | gga | tta | gag | ggt | 1746 |

```
Ser Ala Ile Thr Phe Trp Thr Val Gly Leu Ser Gly Gly Leu Glu Gly
        535                 540                 545 ttt gtc ttc tat tgc ctc cta atc tat gcc tcc ttt tgg tct gga tct    1794
Phe Val Phe Tyr Cys Leu Leu Ile Tyr Ala Ser Phe Trp Ser Gly Ser
        550                 555                 560 tcc gtc gtt acc ttt ata tcc ggt gtt gtt ccg aat atc atg tta tgt    1842
Ser Val Val Thr Phe Ile Ser Gly Val Val Pro Asn Ile Met Leu Cys
565                 570                 575                 580 tac atg gtc tcc att acc tat ctc gcc tac tgt tta ctg ttg agt gga    1890
Tyr Met Val Ser Ile Thr Tyr Leu Ala Tyr Cys Leu Leu Leu Ser Gly
                585                 590                 595 ttc tac gtc aac cga gat cga ata ccg ttt tat tgg acg tgg ttt cat    1938
Phe Tyr Val Asn Arg Asp Arg Ile Pro Phe Tyr Trp Thr Trp Phe His
            600                 605                 610 tac att tca att ctc aag tat ccg tat gag gct gtc tta atc aac gag    1986
Tyr Ile Ser Ile Leu Lys Tyr Pro Tyr Glu Ala Val Leu Ile Asn Glu
            615                 620                 625 ttt gat gac ccg tct cgt tgt ttt gtt agg ggt gtc cag gtt ttc gac    2034
Phe Asp Asp Pro Ser Arg Cys Phe Val Arg Gly Val Gln Val Phe Asp
        630                 635                 640 agt act ctt ctc ggg gga gtg tct gac tcc ggg aag gtt aag ctc ctt    2082
Ser Thr Leu Leu Gly Gly Val Ser Asp Ser Gly Lys Val Lys Leu Leu
645                 650                 655                 660 gaa act ctc agt aaa tct ctg aga acg aag ata acg gag tcc aca tgc    2130
Glu Thr Leu Ser Lys Ser Leu Arg Thr Lys Ile Thr Glu Ser Thr Cys
                665                 670                 675 ttg agg acg ggg tct gac tta ctt gca caa cag ggt att acg caa ttg    2178
Leu Arg Thr Gly Ser Asp Leu Leu Ala Gln Gln Gly Ile Thr Gln Leu
            680                 685                 690 agc aag tgg gat tgc ttg tgg att acg ttt gct tca ggt ctc ttc ttt    2226
Ser Lys Trp Asp Cys Leu Trp Ile Thr Phe Ala Ser Gly Leu Phe Phe
            695                 700                 705 agg atc tta ttt tac ttc gcc ttg ctg ttt ggg agc agg aat aag agg    2274
Arg Ile Leu Phe Tyr Phe Ala Leu Leu Phe Gly Ser Arg Asn Lys Arg
        710                 715                 720 acg tga ggttactact tactagcgcc cacaaataca tttgtgcgca ttagctacat     2330
Thr
725 atttaagtga agcttgaaga attagcttct cgatgttact atacatttgt gaagaagttg  2390 taaaatttat actcatttca tctttgtttc tttaaaagaa tatactgtaa aataaacaag  2450 tatttcttct taaatatcca aattagcatc tgattacttg aatacacatt taaatttcga  2510 ggc                                                                2513

<210> SEQ ID NO 4
<211> LENGTH: 725
<212> TYPE: PRT
<213> ORGANISM: Arabidopsis thaliana

<400> SEQUENCE: 4

Met Asn Leu Ser Leu Ser Gly Arg Lys Ile Ala Met Thr Arg Val Ser
1               5                   10                  15

Ala Glu Thr Gln Tyr Ile Thr Pro Ile Gly Ser Pro Thr Leu Asp Glu
            20                  25                  30

Leu Leu Lys Asp Cys Asp Ser Phe Arg Lys Gly Asp Ser Gly Asp Gly
        35                  40                  45

Val Lys Ser Asp Asp Pro Ala His His Ile Ile Asp Val Glu Ala Leu
    50                  55                  60

Tyr Val Lys Pro Val Pro Tyr Val Leu Asn Phe Asn Asn Leu Gln Tyr
```

-continued

```
            65                  70                  75                  80
Asp Val Thr Leu Arg Arg Phe Gly Phe Ser Arg Gln Asn Gly Val
                    85                  90                  95
Lys Thr Leu Leu Asp Asp Val Ser Gly Glu Ala Ser Asp Gly Asp Ile
                    100                 105                 110
Leu Ala Val Leu Gly Ala Ser Ala Gly Lys Ser Thr Leu Ile Asp
                    115                 120                 125
Ala Leu Ala Gly Arg Val Ala Glu Gly Ser Leu Arg Gly Ser Val Thr
            130                 135                 140
Leu Asn Gly Glu Lys Val Leu Gln Ser Arg Leu Leu Lys Val Ile Ser
145                 150                 155                 160
Ala Tyr Val Met Gln Asp Asp Leu Leu Phe Pro Met Leu Thr Val Lys
                    165                 170                 175
Glu Thr Leu Met Phe Ala Ser Glu Phe Arg Leu Pro Arg Ser Leu Ser
                    180                 185                 190
Lys Ser Lys Lys Met Glu Arg Val Glu Ala Leu Ile Asp Gln Leu Gly
                    195                 200                 205
Leu Arg Asn Ala Ala Asn Thr Val Ile Gly Asp Glu Gly His Arg Gly
            210                 215                 220
Val Ser Gly Gly Glu Arg Arg Arg Val Ser Ile Gly Ile Asp Ile Ile
225                 230                 235                 240
His Asp Pro Ile Val Leu Phe Leu Asp Glu Pro Thr Ser Gly Leu Asp
                    245                 250                 255
Ser Thr Asn Ala Phe Met Val Val Gln Val Leu Lys Arg Ile Ala Gln
                    260                 265                 270
Ser Gly Ser Ile Val Ile Met Ser Ile His Gln Pro Ser Ala Arg Ile
                    275                 280                 285
Val Glu Leu Leu Asp Arg Leu Ile Ile Leu Ser Arg Gly Lys Ser Val
            290                 295                 300
Phe Asn Gly Ser Pro Ala Ser Leu Pro Gly Phe Phe Ser Asp Phe Gly
305                 310                 315                 320
Arg Pro Ile Pro Glu Lys Glu Asn Ile Ser Glu Phe Ala Leu Asp Leu
                    325                 330                 335
Val Arg Glu Leu Glu Gly Ser Asn Glu Gly Thr Lys Ala Leu Val Asp
                    340                 345                 350
Phe Asn Glu Lys Trp Gln Gln Asn Lys Ile Ser Leu Ile Gln Ser Ala
                    355                 360                 365
Pro Gln Thr Asn Lys Leu Asp Gln Asp Arg Ser Leu Ser Leu Lys Glu
            370                 375                 380
Ala Ile Asn Ala Ser Val Ser Arg Gly Lys Leu Val Ser Gly Ser Ser
385                 390                 395                 400
Arg Ser Asn Pro Thr Ser Met Glu Thr Val Ser Ser Tyr Ala Asn Pro
                    405                 410                 415
Ser Leu Phe Glu Thr Phe Ile Leu Ala Lys Arg Tyr Met Lys Asn Trp
                    420                 425                 430
Ile Arg Met Pro Glu Leu Val Gly Thr Arg Ile Ala Thr Val Met Val
                    435                 440                 445
Thr Gly Cys Leu Leu Ala Thr Val Tyr Trp Lys Leu Asp His Thr Pro
            450                 455                 460
Arg Gly Ala Gln Glu Arg Leu Thr Leu Phe Ala Phe Val Pro Thr
465                 470                 475                 480
Met Phe Tyr Cys Cys Leu Asp Asn Val Pro Val Phe Ile Gln Glu Arg
                    485                 490                 495
```

```
Tyr Ile Phe Leu Arg Glu Thr Thr His Asn Ala Tyr Arg Thr Ser Ser
            500                 505                 510

Tyr Val Ile Ser His Ser Leu Val Ser Leu Pro Gln Leu Leu Ala Pro
        515                 520                 525

Ser Leu Val Phe Ser Ala Ile Thr Phe Trp Thr Val Gly Leu Ser Gly
    530                 535                 540

Gly Leu Glu Gly Phe Val Phe Tyr Cys Leu Leu Ile Tyr Ala Ser Phe
545                 550                 555                 560

Trp Ser Gly Ser Ser Val Val Thr Phe Ile Ser Gly Val Val Pro Asn
                565                 570                 575

Ile Met Leu Cys Tyr Met Val Ser Ile Thr Tyr Leu Ala Tyr Cys Leu
            580                 585                 590

Leu Leu Ser Gly Phe Tyr Val Asn Arg Asp Arg Ile Pro Phe Tyr Trp
        595                 600                 605

Thr Trp Phe His Tyr Ile Ser Ile Leu Lys Tyr Pro Tyr Glu Ala Val
    610                 615                 620

Leu Ile Asn Glu Phe Asp Asp Pro Ser Arg Cys Phe Val Arg Gly Val
625                 630                 635                 640

Gln Val Phe Asp Ser Thr Leu Leu Gly Gly Val Ser Asp Ser Gly Lys
                645                 650                 655

Val Lys Leu Leu Glu Thr Leu Ser Lys Ser Leu Arg Thr Lys Ile Thr
            660                 665                 670

Glu Ser Thr Cys Leu Arg Thr Gly Ser Asp Leu Leu Ala Gln Gln Gly
        675                 680                 685

Ile Thr Gln Leu Ser Lys Trp Asp Cys Leu Trp Ile Thr Phe Ala Ser
    690                 695                 700

Gly Leu Phe Phe Arg Ile Leu Phe Tyr Phe Ala Leu Leu Phe Gly Ser
705                 710                 715                 720

Arg Asn Lys Arg Thr
                725

<210> SEQ ID NO 5
<211> LENGTH: 2163
<212> TYPE: DNA
<213> ORGANISM: Arabidopsis thaliana
<220> FEATURE:
<221> NAME/KEY: CDS
<222> LOCATION: (1)..(2163)

<400> SEQUENCE: 5 atg gag att att agc tca tct ttg act tta ggc caa ctt ctc aag aac     48
Met Glu Ile Ile Ser Ser Ser Leu Thr Leu Gly Gln Leu Leu Lys Asn
1               5                   10                  15 gtt agc gac gtt cgt aag gtt gaa gtt ggt gac gaa act cct gtt cat     96
Val Ser Asp Val Arg Lys Val Glu Val Gly Asp Glu Thr Pro Val His
            20                  25                  30 gaa ttc ttt gac agg gat ggt tct tca ctt gac gga gat aat gat cat    144
Glu Phe Phe Asp Arg Asp Gly Ser Ser Leu Asp Gly Asp Asn Asp His
        35                  40                  45 ctt atg cgt cct gtt cct ttc gtt cta tct ttc aac aac ctt act tac    192
Leu Met Arg Pro Val Pro Phe Val Leu Ser Phe Asn Asn Leu Thr Tyr
    50                  55                  60 aac gtc tct gtt cgc cgg aaa ctt gac ttt cac gac ctg gtt cca tgg    240
Asn Val Ser Val Arg Arg Lys Leu Asp Phe His Asp Leu Val Pro Trp
65                  70                  75                  80 agg agg aca tct ttc tcc aag acc aag act ctt cta gac aat atc tcc    288
Arg Arg Thr Ser Phe Ser Lys Thr Lys Thr Leu Leu Asp Asn Ile Ser
                85                  90                  95
```

```
ggt gag act cgt gac gga gag att ctt gcc gtt ctt gga gct agc ggg         336
Gly Glu Thr Arg Asp Gly Glu Ile Leu Ala Val Leu Gly Ala Ser Gly
        100                 105                 110 tca ggt aaa tcc act ttg atc gac gct tta gcg aat cgg atc gct aaa         384
Ser Gly Lys Ser Thr Leu Ile Asp Ala Leu Ala Asn Arg Ile Ala Lys
            115                 120                 125 gga agc ttg aag ggc acg gta acg ctt aac gga gaa gct ctt caa tct         432
Gly Ser Leu Lys Gly Thr Val Thr Leu Asn Gly Glu Ala Leu Gln Ser
        130                 135                 140 cgg atg ctg aaa gtt atc tca gct tat gta atg caa gac gat ctt ctc         480
Arg Met Leu Lys Val Ile Ser Ala Tyr Val Met Gln Asp Asp Leu Leu
145                 150                 155                 160 ttc ccg atg ctt act gtg gaa gaa acc tta atg ttt gca gct gag ttt         528
Phe Pro Met Leu Thr Val Glu Glu Thr Leu Met Phe Ala Ala Glu Phe
                165                 170                 175 cga tta cca aga agc tta cct aaa tcc aag aag aag ctt cga gtt caa         576
Arg Leu Pro Arg Ser Leu Pro Lys Ser Lys Lys Lys Leu Arg Val Gln
            180                 185                 190 gcc cta atc gac cag tta ggg ata aga aac gct gct aaa aca atc att         624
Ala Leu Ile Asp Gln Leu Gly Ile Arg Asn Ala Ala Lys Thr Ile Ile
        195                 200                 205 gga gac gaa gga cac cgt gga atc tcc ggt gga gaa aga agg cga gtt         672
Gly Asp Glu Gly His Arg Gly Ile Ser Gly Gly Glu Arg Arg Arg Val
210                 215                 220 tcg atc gga atc gat atc atc cac gac ccg att gtt ctc ttc ctc gac         720
Ser Ile Gly Ile Asp Ile Ile His Asp Pro Ile Val Leu Phe Leu Asp
225                 230                 235                 240 gaa cct act tct ggt tta gat tcc aca agt gct ttc atg gtg gtt aaa         768
Glu Pro Thr Ser Gly Leu Asp Ser Thr Ser Ala Phe Met Val Val Lys
                245                 250                 255 gta ttg aag aga atc gca gag agt ggc agt atc att ata atg tca ata         816
Val Leu Lys Arg Ile Ala Glu Ser Gly Ser Ile Ile Ile Met Ser Ile
            260                 265                 270 cat cag cca agt cac aga gtt ctc agt tta ctt gat cgt ctt atc ttc         864
His Gln Pro Ser His Arg Val Leu Ser Leu Leu Asp Arg Leu Ile Phe
        275                 280                 285 ttg tca cgt gga cac acc gtc ttt agt ggt tct ccg gcg agt cta ccg         912
Leu Ser Arg Gly His Thr Val Phe Ser Gly Ser Pro Ala Ser Leu Pro
290                 295                 300 agc ttt ttc gcc ggg ttc ggt aat ccg ata ccg gaa aac gag aat caa         960
Ser Phe Phe Ala Gly Phe Gly Asn Pro Ile Pro Glu Asn Glu Asn Gln
305                 310                 315                 320 acg gag ttt gca ctc gat cta atc aga gaa ctc gaa gga tca gct gga        1008
Thr Glu Phe Ala Leu Asp Leu Ile Arg Glu Leu Glu Gly Ser Ala Gly
                325                 330                 335 gga aca aga gga tta gtt gaa ttc aac aag aaa tgg caa gag atg aag        1056
Gly Thr Arg Gly Leu Val Glu Phe Asn Lys Lys Trp Gln Glu Met Lys
            340                 345                 350 aaa cag agc aat cct caa acc cta act ccg ccg gct tct cca aac cca        1104
Lys Gln Ser Asn Pro Gln Thr Leu Thr Pro Pro Ala Ser Pro Asn Pro
        355                 360                 365 aat tta acc ttg aaa gaa gcg att tcc gcc agc ata agc aga gga aaa        1152
Asn Leu Thr Leu Lys Glu Ala Ile Ser Ala Ser Ile Ser Arg Gly Lys
        370                 375                 380 cta gtc tcc ggt ggc ggc ggt ggt tcc tcc gtc ata aac cac ggt ggc        1200
Leu Val Ser Gly Gly Gly Gly Gly Ser Ser Val Ile Asn His Gly Gly
385                 390                 395                 400 gga acc tta gcc gtc cct gca ttc gcg aat ccg ttc tgg atc gaa atc        1248
Gly Thr Leu Ala Val Pro Ala Phe Ala Asn Pro Phe Trp Ile Glu Ile
                405                 410                 415
```

| | |
|---|---|
| aaa act ctc acc aga cgc tca atc ctc aac tcc cga cga caa ccg gag<br>Lys Thr Leu Thr Arg Arg Ser Ile Leu Asn Ser Arg Arg Gln Pro Glu<br>              420                 425                 430 | 1296 |
| cta ctc gga atg cga tta gcc acc gta atc gtc acc gga ttc atc tta<br>Leu Leu Gly Met Arg Leu Ala Thr Val Ile Val Thr Gly Phe Ile Leu<br>     435                 440                 445 | 1344 |
| gcc acc gta ttc tgg cga ttg gat aat tca cca aaa gga gtt caa gag<br>Ala Thr Val Phe Trp Arg Leu Asp Asn Ser Pro Lys Gly Val Gln Glu<br> 450                 455                 460 | 1392 |
| cgg tta ggg ttc ttc gca ttc gca atg tca aca atg ttc tac act tgc<br>Arg Leu Gly Phe Phe Ala Phe Ala Met Ser Thr Met Phe Tyr Thr Cys<br>465                 470                 475                 480 | 1440 |
| gcc gat gct ctt ccc gtg ttc ctc cag gaa cgt tac atc ttc atg aga<br>Ala Asp Ala Leu Pro Val Phe Leu Gln Glu Arg Tyr Ile Phe Met Arg<br>                485                 490                 495 | 1488 |
| gaa aca gct tac aac gct tac cgg aga tcc tcc tac gtt ctc tct cac<br>Glu Thr Ala Tyr Asn Ala Tyr Arg Arg Ser Ser Tyr Val Leu Ser His<br>        500                 505                 510 | 1536 |
| gcc att gtt acc ttc cct tcg ctc atc ttc ctc tct tta gct ttc gca<br>Ala Ile Val Thr Phe Pro Ser Leu Ile Phe Leu Ser Leu Ala Phe Ala<br>            515                 520                 525 | 1584 |
| gtg acg acg ttt tgg gct gtt ggg ctt gaa gga ggc cta atg ggc ttt<br>Val Thr Thr Phe Trp Ala Val Gly Leu Glu Gly Gly Leu Met Gly Phe<br>   530                 535                 540 | 1632 |
| tta ttc tac tgc tta atc atc tta gcc tct ttc tgg tcc gga agc tcc<br>Leu Phe Tyr Cys Leu Ile Ile Leu Ala Ser Phe Trp Ser Gly Ser Ser<br>545                 550                 555                 560 | 1680 |
| ttc gtg act ttc tta tcc ggc gtc gtt cca cat gtg atg tta ggc tac<br>Phe Val Thr Phe Leu Ser Gly Val Val Pro His Val Met Leu Gly Tyr<br>                565                 570                 575 | 1728 |
| acg atc gtt gtt gct att tta gct tac ttc ttg ctt ttc agt ggc ttc<br>Thr Ile Val Val Ala Ile Leu Ala Tyr Phe Leu Leu Phe Ser Gly Phe<br>        580                 585                 590 | 1776 |
| ttc atc aac aga gat cga atc cct cag tat tgg att tgg ttt cat tat<br>Phe Ile Asn Arg Asp Arg Ile Pro Gln Tyr Trp Ile Trp Phe His Tyr<br>            595                 600                 605 | 1824 |
| ctt tct ctg gtt aag tat cca tac gag gcg gtt ctt cag aac gag ttc<br>Leu Ser Leu Val Lys Tyr Pro Tyr Glu Ala Val Leu Gln Asn Glu Phe<br>   610                 615                 620 | 1872 |
| tcg gat cct aca gaa tgt ttt gtg aga ggt gtt cag ctt ttc gac aac<br>Ser Asp Pro Thr Glu Cys Phe Val Arg Gly Val Gln Leu Phe Asp Asn<br>625                 630                 635                 640 | 1920 |
| tcg cct ttg gga gaa ttg acg tat ggg atg aag ctg agg ctt ttg gat<br>Ser Pro Leu Gly Glu Leu Thr Tyr Gly Met Lys Leu Arg Leu Leu Asp<br>                645                 650                 655 | 1968 |
| tct gtg agc cgg tcg ata ggt atg agg ata tcg agc tct acg tgt tta<br>Ser Val Ser Arg Ser Ile Gly Met Arg Ile Ser Ser Ser Thr Cys Leu<br>        660                 665                 670 | 2016 |
| acg acg ggt gct gat gtt ctg aag cag caa gga gtg aca cag ctt agt<br>Thr Thr Gly Ala Asp Val Leu Lys Gln Gln Gly Val Thr Gln Leu Ser<br>            675                 680                 685 | 2064 |
| aaa tgg aac tgc ttg ctt atc acg gta ggt ttc gga ttc cta ttt agg<br>Lys Trp Asn Cys Leu Leu Ile Thr Val Gly Phe Gly Phe Leu Phe Arg<br>   690                 695                 700 | 2112 |
| att ttg ttt tac ttg tgt ttg ttg ctt ggg agc aaa aac aag agg agg<br>Ile Leu Phe Tyr Leu Cys Leu Leu Leu Gly Ser Lys Asn Lys Arg Arg<br>705                 710                 715                 720 | 2160 |
| tga | 2163 |

<210> SEQ ID NO 6

<211> LENGTH: 720
<212> TYPE: PRT
<213> ORGANISM: Arabidopsis thaliana

<400> SEQUENCE: 6

```
Met Glu Ile Ile Ser Ser Leu Thr Leu Gly Gln Leu Leu Lys Asn
1               5                   10                  15

Val Ser Asp Val Arg Lys Val Glu Val Gly Asp Glu Thr Pro Val His
            20                  25                  30

Glu Phe Phe Asp Arg Asp Gly Ser Leu Asp Gly Asp Asn Asp His
        35                  40                  45

Leu Met Arg Pro Val Pro Phe Val Leu Ser Phe Asn Asn Leu Thr Tyr
    50                  55                      60

Asn Val Ser Val Arg Arg Lys Leu Asp Phe His Asp Leu Val Pro Trp
65                  70                  75                  80

Arg Arg Thr Ser Phe Ser Lys Thr Lys Thr Leu Leu Asp Asn Ile Ser
                85                  90                  95

Gly Glu Thr Arg Asp Gly Glu Ile Leu Ala Val Leu Gly Ala Ser Gly
                100                 105                 110

Ser Gly Lys Ser Thr Leu Ile Asp Ala Leu Ala Asn Arg Ile Ala Lys
            115                 120                 125

Gly Ser Leu Lys Gly Thr Val Thr Leu Asn Gly Glu Ala Leu Gln Ser
        130                 135                 140

Arg Met Leu Lys Val Ile Ser Ala Tyr Val Met Gln Asp Asp Leu Leu
145                 150                 155                 160

Phe Pro Met Leu Thr Val Glu Glu Thr Leu Met Phe Ala Ala Glu Phe
                165                 170                 175

Arg Leu Pro Arg Ser Leu Pro Lys Ser Lys Lys Leu Arg Val Gln
                180                 185                 190

Ala Leu Ile Asp Gln Leu Gly Ile Arg Asn Ala Ala Lys Thr Ile Ile
            195                 200                 205

Gly Asp Glu Gly His Arg Gly Ile Ser Gly Gly Glu Arg Arg Arg Val
        210                 215                 220

Ser Ile Gly Ile Asp Ile Ile His Asp Pro Ile Val Leu Phe Leu Asp
225                 230                 235                 240

Glu Pro Thr Ser Gly Leu Asp Ser Thr Ser Ala Phe Met Val Val Lys
                245                 250                 255

Val Leu Lys Arg Ile Ala Glu Ser Gly Ser Ile Ile Met Ser Ile
                260                 265                 270

His Gln Pro Ser His Arg Val Leu Ser Leu Leu Asp Arg Leu Ile Phe
            275                 280                 285

Leu Ser Arg Gly His Thr Val Phe Ser Gly Ser Pro Ala Ser Leu Pro
        290                 295                 300

Ser Phe Phe Ala Gly Phe Gly Asn Pro Ile Pro Glu Asn Glu Asn Gln
305                 310                 315                 320

Thr Glu Phe Ala Leu Asp Leu Ile Arg Glu Leu Glu Gly Ser Ala Gly
                325                 330                 335

Gly Thr Arg Gly Leu Val Glu Phe Asn Lys Lys Trp Gln Glu Met Lys
            340                 345                 350

Lys Gln Ser Asn Pro Gln Thr Leu Thr Pro Pro Ala Ser Pro Asn Pro
        355                 360                 365

Asn Leu Thr Leu Lys Glu Ala Ile Ser Ala Ser Ile Ser Arg Gly Lys
    370                 375                 380

Leu Val Ser Gly Gly Gly Gly Ser Ser Val Ile Asn His Gly Gly
385                 390                 395                 400
```

-continued

```
Gly Thr Leu Ala Val Pro Ala Phe Ala Asn Pro Phe Trp Ile Glu Ile
            405                 410                 415
Lys Thr Leu Thr Arg Arg Ser Ile Leu Asn Ser Arg Arg Gln Pro Glu
            420                 425                 430
Leu Leu Gly Met Arg Leu Ala Thr Val Ile Val Thr Gly Phe Ile Leu
            435                 440                 445
Ala Thr Val Phe Trp Arg Leu Asp Asn Ser Pro Lys Gly Val Gln Glu
    450                 455                 460
Arg Leu Gly Phe Phe Ala Phe Ala Met Ser Thr Met Phe Tyr Thr Cys
465                 470                 475                 480
Ala Asp Ala Leu Pro Val Phe Leu Gln Glu Arg Tyr Ile Phe Met Arg
                485                 490                 495
Glu Thr Ala Tyr Asn Ala Tyr Arg Arg Ser Ser Tyr Val Leu Ser His
                500                 505                 510
Ala Ile Val Thr Phe Pro Ser Leu Ile Phe Leu Ser Leu Ala Phe Ala
            515                 520                 525
Val Thr Thr Phe Trp Ala Val Gly Leu Glu Gly Gly Leu Met Gly Phe
    530                 535                 540
Leu Phe Tyr Cys Leu Ile Ile Leu Ala Ser Phe Trp Ser Gly Ser Ser
545                 550                 555                 560
Phe Val Thr Phe Leu Ser Gly Val Val Pro His Val Met Leu Gly Tyr
                565                 570                 575
Thr Ile Val Val Ala Ile Leu Ala Tyr Phe Leu Leu Phe Ser Gly Phe
                580                 585                 590
Phe Ile Asn Arg Asp Arg Ile Pro Gln Tyr Trp Ile Trp Phe His Tyr
            595                 600                 605
Leu Ser Leu Val Lys Tyr Pro Tyr Glu Ala Val Leu Gln Asn Glu Phe
    610                 615                 620
Ser Asp Pro Thr Glu Cys Phe Val Arg Gly Val Gln Leu Phe Asp Asn
625                 630                 635                 640
Ser Pro Leu Gly Glu Leu Thr Tyr Gly Met Lys Leu Arg Leu Leu Asp
                645                 650                 655
Ser Val Ser Arg Ser Ile Gly Met Arg Ile Ser Ser Ser Thr Cys Leu
                660                 665                 670
Thr Thr Gly Ala Asp Val Leu Lys Gln Gln Gly Val Thr Gln Leu Ser
            675                 680                 685
Lys Trp Asn Cys Leu Leu Ile Thr Val Gly Phe Gly Phe Leu Phe Arg
    690                 695                 700
Ile Leu Phe Tyr Leu Cys Leu Leu Leu Gly Ser Lys Asn Lys Arg Arg
705                 710                 715                 720
```